United States Patent
Plant et al.

(10) Patent No.: US 6,770,595 B2
(45) Date of Patent: Aug. 3, 2004

(54) CYCLIC IMINES AS PESTICIDES

(75) Inventors: Andrew Plant, Leverkusen (DE); Gerd Kleefeld, Neuss-Üdesheim (DE); Thorsten Pötter, Köln (DE); Christoph Erdelen, Leichlingen (DE); Norbert Mencke, Leverkusen (DE); Andreas Turberg, Iiaan (DE); Ulrike Wachendorff-Neumann, Neuwied (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/028,648

(22) Filed: Dec. 19, 2001

(65) Prior Publication Data

US 2002/0151571 A1 Oct. 17, 2002

Related U.S. Application Data

(62) Division of application No. 09/659,041, filed on Sep. 9, 2000, now Pat. No. 6,399,771, which is a division of application No. 09/297,964, filed on May 11, 1999, now Pat. No. 6,274,613.

(30) Foreign Application Priority Data

Nov. 20, 1996 (DE) .......................... 196 48 011

(51) Int. Cl.$^7$ ........................ A01N 43/46; C07D 223/04
(52) U.S. Cl. ...................... 504/218; 504/248; 540/609; 546/236
(58) Field of Search ............................. 504/218, 248; 540/609; 546/236

(56) References Cited

FOREIGN PATENT DOCUMENTS

| WO | 91/29268 | 12/1994 |
|---|---|---|
| WO | 94/29268 | * 12/1994 |

OTHER PUBLICATIONS

Organic Preparations and Procedures International, vol. 25, No. 2, (month unavailable) 1993.
Wei et al, A Practical Procedure for the Synthesis of 5–Substituted γ–Lactams, pp. 255–258.
J. Org. Chem., 56 (month unavailable) 1991, pp. 1822–1827, Savoia et al, Organometallic.
Reactions of ωHeterosubstituted N–Acyl Lactams. A New Route to γ–Keto Aldehydes from 5–Ethoxy-2–pyrrolidinone.
Synthesis, Apr. 1980, pp. 315–317, Eine einfache Herstellung von ω–Alkoxylactamen durch anodische Alkoxylierung, Michael Mitzlaff et al.
Chem. Ber 12. (month unavailable) 1987. p. 285–290. Mormann et al. "Synthese und Stabilisierung von Isocyanatoketenen".

* cited by examiner

*Primary Examiner*—Joseph K. McKane
*Assistant Examiner*—Sonya Wright
(74) *Attorney, Agent, or Firm*—Richard E.L. Henderson; Raymond J. Harmuth

(57) ABSTRACT

The invention relates to novel cyclic imines of the formula (I)

$$Ar^1 \underset{(CH_2)_n}{\overset{N}{\diagup\diagdown}} Ar^2, \qquad (I)$$

in which
$Ar^1$ and $Ar^2$ each represent substituted phenyl and
n represents 1, 2 or 3,
to a plurality of processes for their preparation and to their use as pesticides.

8 Claims, No Drawings

CYCLIC IMINES AS PESTICIDES

This is a divisional application of U.S. patent application Ser. No. 09/659,041, filed Sep. 9, 2000, now U.S. Pat. No. 6,399,771 which is in turn a divisional application of U.S. patent application Ser. No. 09/297,964, filed May 11, 1999, now U.S. Pat. No. 6,274,613 B1 issued Aug. 14, 2001, which U.S. patent issued on a continued prosecution application filed under 37 C.F.R. 1.53(d)

TECHNICAL FIELD OF THE INVENTION

The invention relates to novel cyclic imines, to a plurality of processes for their preparation and to their use as pesticides.

BACKGROUND OF THE INVENTION

Only few substituted cyclic α,α'-diphenylimines have been disclosed before three 2,5-diphenyl-1-pyrrolines alkoxy-substituted on the 2-phenyl ring [5-(2,5-(dimethoxyphenyl)-2-phenyl-3,4-dihydro-2H-pyrrole and 5-(4-methoxyphenyl)-2-phenyl-3,4-dihydro-2H-pyrrole in Chem. Ber 96, 93 (1963) and the corresponding 4-propoxy compound in J. Prakt. Chem, Series 4, 1, 57 (1955)] and the unsubstituted 2,6-diphenyl-3,4,5,6-tetrahydropyridine [cf. for example Bull Soc Chim Fr. 1974, 258, and Chem Ber. 116, 3931 (1983)].

Nothing is known about their suitability for use as pesticides.

DETAILED DESCRIPTION OF THE INVENTION

This invention, accordingly, provides novel cyclic imines of the formula (I)

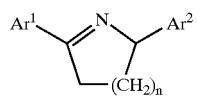

(I)

in which
n represents 1, 2 or 3,
$Ar^1$ represents the radical

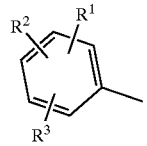

and
$Ar^2$ represents the radical

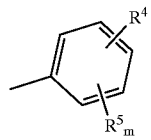

in which
m represents 0, 1, 2, 3 or 4,
$R^1$ represents halogen, cyano, nitro, alkyl, alkoxy, halogenoalkyl, halogenoalkoxy, alkoxyalkyl, $-S(O)_oR^6$ or $-N^7R^8$, $R^2$ and $R^3$ independently of one another each represent hydrogen, halogen, cyano, nitro, alkyl, alkoxy, halogenoalkyl, halogenoalkoxy, alkoxyalkyl, $-S(O)_oR^6$, or $-NR^7R^8$,
$R^4$ represents halogen, cyano, trialkylsilyl, $-CO-NR^{10}R^{11}$, tetrahydropyranyl or one of the groupings below
(l) $-X-A$.
(m) $-B-Z-D$
(n) $-Y-E$,
$R^5$ represents hydrogen, halogen, cyano, nitro, alkyl, alkoxy, halogenoalkyl, halogenoalkoxy, alkoxyalkoxy or $-S(O)_oR^6$,
o represents 0, 1 or 2,
$R^6$ represents alkyl or halogenoalkyl,
$R^7$ and $R^8$ independently of one another each represent hydrogen or alkyl, together represent alkylene,
$R^{10}$ and $R^{11}$ independently of one another each represent hydrogen, alkyl, halogenoalkyl or represent phenyl or phenylalkyl, each of which is optionally mono- or polysubstituted by radicals from the list $W^1$,
X represents a direct bond, oxygen, sulphur, carbonyl, carbonyloxy, oxycarbonyl, alkylene, alkenylene, alkenylene, alkyleneoxy, oxyalkylene, thioalkylene, alkylenedioxy or dialkylsilylene,
A represents phenyl, naphthyl or tetrahydronaphthyl, each of which is optionally mono- or polysubstituted by radicals from the list $W^1$, or represents 5 to 10-membered heterocyclyl having one or more hetero atoms from the group consisting of nitrogen, oxygen and sulphur and containing 1 or 2 aromatic rings, which is optionally mono- or polysubstituted by radicals from the list $W^2$,
B represents p-phenylene which is optionally mono- or disubstituted by radicals from the list WI,
Z represents oxygen or sulphur,
D represents hydrogen, alkyl, alkenyl, alkinyl, halogenoalkyl, halogenoalkenyl, respectively optionally halogen-, alkyl-, alkenyl-, halogenoalkenyl-, phenyl-, styryl-, halogenophenyl- or halogenostyryl-substituted cycloalkyl or cycloalkylalkyl, represents respectively optionally halogen- or alkyl-substituted cycloalkenyl or cycloalkenylalkyl, represents respectively optionally nitro-, halogen-, alkyl-, alkoxy-, halogenoalkyl- or halogenoalkoxy-substituted phenylalkyl, naphthylalkyl, tetrahydronaphthylalkyl or 5- or 6-membered hetarylalkyl having 1 or 2 hetero atoms from the group consisting of nitrogen, oxygen and sulphur, represents $-CO-R^{12}$, $-CO-NR^{13}R^{14}$, or represents the grouping $-(CH_2)_p-(CR^{15}R^{16})_q-(CH_2)_r-G$, or
Z and D together represent optionally nitro-, halogen-, alkyl-, alkoxy-, haloogenoalkyl- or halogenoalkoxy-substituted phenoxyalkyl,
Y represents a direct bond, oxygen, sulphur, carbonyl, carbonyloxy, oxycarbonyl, alkylene, alkenylene, alkenylene, alkyleneoxy, oxyalkylene, thioalkylene, alkylenedioxy or represents p-phenylene which is optionally mono- or disubstituted by radicals from the list $W^1$,
E represents hydrogen, alkyl, alkenyl, alkinyl, halogenoalkyl, halogenoalkenyl, respectively optionally halogen-, alkyl-, alkenyl-, halogenoalkenyl-, phenyl-, styryl-, halogenophenyl- or halogenostyryl-substituted cycloalkyl, represents respectively optionally halogen- or alkyl-substituted cycloalkenyl, represents phenyl which is optionally mono- to tetrasubstituted by radicals from the list W¹ or represents 5- or 6-membered hetaryl having 1 or 2 hetero atoms from the group consisting of nitrogen, oxygen and sulphur, which is optionally mono- to tetra-substituted by radicals from the list W², or represents the grouping —(CH₂)$_p$—(CR¹⁵R¹⁶)$_q$—(CH₂)$_r$—G, R¹² represents alkyl, alkoxy, alkenyl, alkenyloxy, respectively optionally halogen-, alkyl-, alkenyl-, halogenoalkyl- or halogenoalkenyl-substituted cycloalkyl, cycloalkytoxy or cycloalkylalkyloxy or represents respectively optionally nitro-, halogen-, alkyl-, alkoxy-, halogenoalkyl- or halogenoalkoxy-substituted phenyl or naphthyl, R¹³ represents hydrogen or alkyl, R¹⁴ represents alkyl, halogenoalkyl, respectively optionally halogen-, alkyl-, alkenyl-, halogenoalkyl- or halogenoalkenyl-substituted cycloalkyl or cycloalkylalkyl or represents respectively optionally halogen-, alkyl-, alkoxy-, halogenoalkyl- or halogenoalkoxy-substituted phenyl or phenylalkyl, p, q and r independently of one another each represent 0, 1, 2 or 3, their sum being smaller than 6, R¹⁵ and R¹⁶ independently of one another each represent hydrogen or alkyl, G represents cyano, represents a 5- or 6-membered heterocycle having 1 to 3 identical or different hetero atoms from the group consisting of nitrogen, oxygen and sulphur, which is optionally substituted by halogen, alkyl or halogenoalkyl and, at the attachment point, optionally by the radical R¹⁷, or represents one of the groupings below —CO—R¹⁷ (a)

—CO—OR¹⁸ (b)

—CO—NR¹⁹R²⁰ (c)

—CS—NR¹⁹R²⁰ (d)

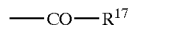 (e)

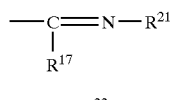 (f)

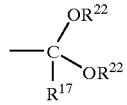 (g)

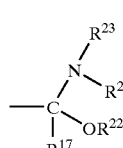 (h)

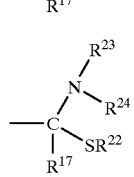 (i)

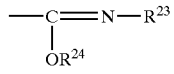 (j)

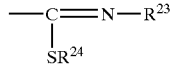 (k)

R¹⁷ represents hydrogen, alkyl, alkenyl, halogenoalkyl, halogenoalkenyl, optionally halogen-, alkyl- or halogenoalkyl-substituted cycloalkyl, or represents phenyl which is optionally mono- to pentasubstituted by alkylcarbonylamino, alkylcarbonylalkylamino and/or radicals from the list W³, R¹⁸ represents hydrogen, alkyl, alkenyl, halogenoalkyl, halogenoalkenyl, respectively optionally halogen-, alkyl- or halogenoalkyl-substituted cycloalkyl or cycloalkylalkyl or represents arylalkyl which is optionally mono- to pentasubstituted by radicals from the list W¹, R¹⁹ and R²⁰ independently of one another each represent hydrogen, alkyl, alkenyl, haloogenoalkyl, halogenoalkenyl, alkoxy, respectively optionally halogen-, alkyl- or halogenoalkyl-substituted cycloalkyl or cycloalkylalkyl, represent aryl or arylalkyl, each of which is optionally mono- to pentasubstituted by radicals from the list W³, represent —OR¹⁸ or —NR¹⁷R¹⁸ or together represent an alkylene chain having 2 to 6 members in which one methylene group is optionally replaced by oxygen, R²¹ represents —OR¹⁸, —NR¹⁷R¹⁸ or —N(R¹⁷)—COOR¹⁸, R²², R²³ and R²⁴ independently of one another each represent alkyl, W¹ represents hydrogen, halogen, cyano, formyl, nitro, alkyl, trialkylsilyl, alkoxy, halogenoalkyl, halogenoalkoxy, halogenoalkenyloxy, alkylcarbonyl, alkoxycarbonyl, pentafluorothio or —S(O)OR⁶, W² represents halogen, cyano, formyl, nitro, alkyl, trialkylsilyl, alkoxy, halogenoalkyl, halogenoalkoxy, alkylcarbonyl, alkoxycarbonyl, pentafluorothio, —S(O)$_o$R⁶ or —C(R¹⁷)=N—R²¹, W³ represents halogen, cyano, nitro, alkyl, alkoxy, halogenoalkyl, halogenoalkoxy, dialkylamino —S(O)$_o$R⁶, —COOR²⁵ or —CONR²⁶R²⁷, R²⁵ represents hydrogen, alkyl, halogenoalkyl, optionally halogen-, alkyl- or halogenoalkyl-substituted cycloalkyl or represents phenyl which is optionally mono- to penta-substituted by radicals from the list W⁴, R²⁶ and R²⁷ independently of one another each represent hydrogen, alkyl, alkenyl, halogenoalkyl, halogenoalkenyl, alkoxy, respectively optionally halogen-, alkyl- or halogenoalkyl-substituted cycloalkyl or cycloalkylalkyl or represent aryl or arylalkyl, each of which is optionally mono- to penta-substituted by radicals from the list W⁴, represent —OR²² or —NR²³R²⁴ or together represent an alkylene chain having 2 to 6 members in which one methylene group is optionally replaced by oxygen, and W⁴ represents halogen, cyano, nitro, alkyl, alkoxy, halogenoalkyl, halogenoalkoxy, dialkylamino, alkoxycarbonyl, dialkylaminocarbonyl or —S(O)$_o$R⁶.

Also depending on the kind of substituents, the compounds of the formula (I) may be present as geometrical and/or optical isomers or as mixtures of isomers in varying composition which can, if appropriate, be separated in a conventional manner. The present invention provides the pure isomers and also the mixtures of isomers, their preparation and use and compositions comprising them. Below, reference is always made to compounds of the formula (I) for simplicity, although the pure compounds and also, if appropriate, mixtures of varying proportions of isomeric compounds are meant.

Furthermore, it has been found that the novel compounds of the formula (I) are obtained by one of the processes described below.

A) Cyclic imines of the formula (I)

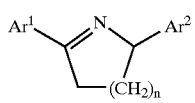
(I)

In which
$Ar^1$, $Ar^2$ and n are each as defined above
are obtained by cyclocondensing aminoketones of the formula (II)

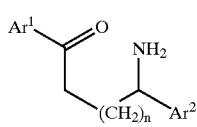
(II)

in which
$Ar^1$, $Ar^2$ and n are each as defined above,
or preferably acidic salts thereof, optionally in the presence of an acid binder.

B) Cyclic imines of the formula (I) can also be prepared by reacting cyclic O-methylsulphonyl oximes of the formula (III)

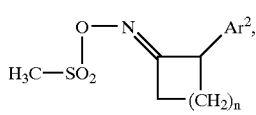
(III)

in which
$Ar^2$ and n are each as defined above
with aryl Grignard compounds of the formula (IV)

$AR^1$-Mg-Hal (IV)

in which
$Ar^1$ is as defined above and
Hal represents chlorine, bromine or iodine,
in the presence of a diluent.

C) Cyclic imines of the formula (I-b)

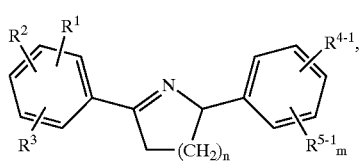
(I-b)

in which
$R^1$, $R^2$, $R^3$, n and m are each as defined above,
$R^{4-1}$ represents A or one of the groupings below —B—Z—D (m)

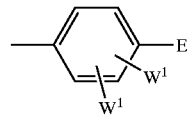
(n-a)

where
A, B, D, E, $W^1$ and Z are each as defined above and
$R^{5-1}$ represents hydrogen, fluorine, cyano, nitro, alkyl, alkoxy, halogenoalkyl, halogenoalkoxy, alkoxyalkoxy or —$SR^6$ where
$R^6$ is as defined above
can be prepared by coupling compounds of the formula (V)

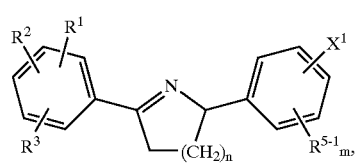
(V)

in which
$R^1$, $R^2$, $R^3$, $R^{5-1}$, n and m are each as defined above and
$X^1$ represents bromine, iodine or —$OSO_2CF_3$
with boronic acids of the formula (VI)

$R^{4-1}$—$B(OH)_2$ (VI)

in which
$R^{4-1}$ is as defined above,
in the presence of a catalyst and in the presence of an acid binder and in the presence of a solvent.

D) Cyclic imines of the formula (I-c)

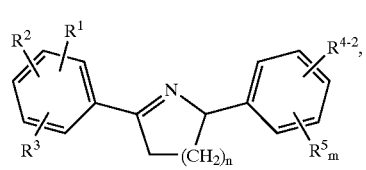
(I-c)

in which
$R^1$, $R^2$, $R^3$, $R^5$, n and m are each as defined above,
$R^{4-2}$ represents one of the groupings below —B—Z—$D^1$ (m-b)

—$Y^1$—$E^1$ (n-b)

in which
B and Z are each as defined above,
$Y^1$ represents oxygen or sulphur and
$D^1$ and $E^1$ each represent the grouping —$(CH_2)_p$—$(CR^{15}R^{16})_q$—$(CH_2)_r$—G in which
$R^{16}$, $R^{16}$, G, p, q and r are each as defined above
can be prepared by condensing cyclic imines of the formula (I-d)

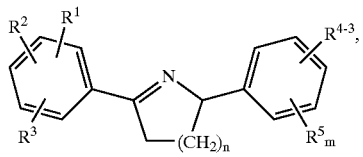 (I-d)

in which

R$^1$, R$^2$, R$^3$, R$^5$, n and m are each as defined above and

R$^{4-3}$ represents one of the groupings below

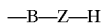 (m-c)

 (n-c)

in which

B, Y$^1$ and Z are each as defined above with compounds of the formula (VII)

 (VII)

in which

R$^{15}$, R$^{16}$, G, p, q and r are each as defined above and

Ab represents a leaving group

E) Cyclic imines of the formula (I-e)

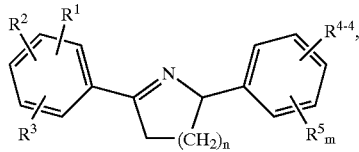 (I-e)

in which

R$^1$, R$^2$, R$^3$, R$^5$, n and m are each as defined above and

R$^{4—4}$ represents a grouping from the description of the compounds of the formula (I) according to the invention containing the radical G where G represents one of the abovementioned groupings (e) to (k)

can be prepared by customary and known derivatizations of the corresponding keto derivatives, carboxylic acid derivatives or nitriles, ie. compounds of the formula (I) in which G represents cyano or one of the groupings (a) to (d).

Furthermore, it has been found that the novel compounds of the formula (1) combine good plant safety with very good activity as pesticides, in particular against arthropods in agriculture but also parasites encountered in animal husbandry and with pets.

The compounds according to the invention are defined in a general way by the formula (I). Preferred substituents or ranges of the radicals listed in the formulae mentioned above and below are illustrated below.

n preferably represents, 1, 2 or 3.

Ar$^1$ preferably represents the radical

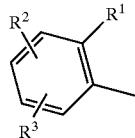

Ar$^2$ preferably represents the radical

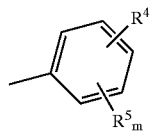

m preferably represents 0, 1, 2 or 3.

R$^1$ preferably represents halogen, cyano, nitro, C$_1$–C$_6$-alkyl, C$_1$–C$_6$-alkoxy, C$_1$–C$_6$-halogenoalkyl or C$_1$–C$_6$-halogenoalkoxy, represents C$_1$–C$_6$-alkoxy-C$_1$–C$_6$-alkyl, —S(O)$_o$R$^6$ or —NR$^7$R$^8$.

R$^2$ and R$^3$ independently of one another each preferably represent hydrogen, halogen, cyano, nitro, C$_1$–C$_6$-alkyl, C$_1$–C$_6$-alkoxy, C$_1$–C$_6$-halogenoalkyl or C$_1$–C$_6$-halogenoalkoxy, represent C$_1$–C$_6$-alkoxy-C$_1$–C$_6$-alkyl, —S(O)$_o$R$^6$ or —NR$^7$R$^8$.

R$^4$ preferably represents a substituent in meta- or paraposition from the group consisting of halogen, cyano, tri-(C$_1$–C$_6$-alkyl)-silyl, —CO—NR$^{10}$R$^{11}$, tetrahydropyranyl or one of the groupings below

 (l)

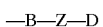 (m)

 (n)

R$^5$ preferably represents hydrogen, halogen, cyano, nitro, C$_1$–C$_{16}$-alkyl, C$_1$–C$_{16}$-alkoxy, C$_1$–C$_6$-halogenoalkyl, C$_1$–C$_6$-halogenoalkoxy, C$_1$–C$_8$-alkoxy-C$_1$–C$_8$-alkoxy or —S(O)OR$^6$.

o preferably represents 0, 1 or 2.

R$^6$ preferably represents optionally fluorine- or chlorine-substituted C$_1$–C$_6$-alkyl.

R$^7$ and R$^8$ independently of one another each preferably represent hydrogen or C$_1$–C$_6$-alkyl, such as, for example, methyl, ethyl, n-propyl, isopropyl, n-butyl, isobutyl, sec-butyl, tert-butyl or together represent C$_2$–C$_5$-alkylene, such as, for example, —(CH$_2$)$_4$— or —(CH$_2$)$_5$—.

R$^{10}$ and R$^{11}$ independently of one another each preferably represent hydrogen, C$_1$–C$_6$-alkyl, C$_1$–C$_6$-halogenoalkyl or represent phenyl or phenyl-C$_1$–C$_4$-alkyl, each of which is optionally mono- to trisubstituted by radicals from the list W$^1$.

X preferably represents a direct bond, oxygen, sulphur, carbonyl, carbonyloxy, oxycarbonyl, C$_1$–C$_4$-alkylene, C$_2$–C$_4$-alkenylene, C$_2$–C$_4$-alkenylene, C$_1$–C$_4$-alkyleneoxy, C$_1$–C$_4$-oxyalkylene, C$_1$–C$_4$-thioalkylene, C$_1$–C$_4$-alkylenedioxy or di-C$_1$–C$_4$-alkylsilylene.

A preferably represents phenyl, naphthyl or tetrahydronaphthyl, each of which is optionally mono- to tetrasubstituted by radicals from the list W$^1$, or represents 5- to 10-membered heterocyclyl having 1 to 4 hetero atoms, including 0 to 4 nitrogen atoms, 0 to 2 oxygen atoms and 0 to 2 sulphur atoms, and containing 1 or 2 aromatic rings, which is in each case optionally mono- to tetrasubstituted by radicals from the list 1 (in particular furyl, benzofuryl, thienyl, benzothienyl, oxazolyl, benzoxazolyl, thiazolyl, benzthiazoyl, pyrrolyl, pyridyl, pyrimidyl, 1,3,5-triazinyl, quinolinyl, isoquinolinyl, indolyl, purinyl, benzodioxolyl, indanyl, benzodioxanyl or chromanyl).

B preferably represents p-phenylene which is optionally mono- or disubstituted by radicals from the list W.

Z preferably represents oxygen or sulphur.

D preferably represents hydrogen, $C_1$–$C_{16}$-alkyl, $C_2$–$C_{16}$-alkenyl, $C_2$–$C_6$-alkinyl, $C_1$–$C_{16}$-halogenoalkyl, $C_2$–$C_{16}$-halogenoalkenyl, respectively optionally halogen-, $C_1$–$C_4$-alkyl-, $C_2$–$C_4$-alkenyl-, $C_2$–$C_4$-haloogenoalkenyl-, phenyl-, styryl-, halogenophenyl- or halogenostyryl-substituted $C_1$–$C_8$-cycloalkyl or $C_3$–$C_8$-cycloalkyl-$C_1$–$C_6$-alkyl, represents respectively optionally halogen- or $C_1$–$C_4$-alkyl-substituted $C_5$–$C_8$-cycloalkenyl or $C_5$–$C_8$-cycloalkenyl-$C_1$–$C_4$-alkyl, represents respectively optionally nitro-, halogen-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl-$C_1$–$C_6$-alkyl, naphthyl-$C_1$–$C_6$-alkyl, tetrahydronaphthyl-$C_1$–$C_6$-alkyl or 5- or 6-membered hetaryl-$C_1$–$C_6$-alkyl having 1 or 2 hetero atoms from the group consisting of nitrogen, oxygen and sulphur (in particular furylmethyl, thienylmethyl, pyrrolylmethyl, oxazolylmethyl, isoxazolylmethyl, thiazolylmethyl or pyridylmethyl), represents —CO—$R^{12}$, —CO—$NR^{13}R^{14}$, or represents the grouping

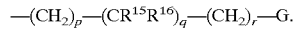

Z and D also preferably together represent optionally nitro-, halogen-, $C_1$–$C_6$-alkyl-, $C_1$–$C_6$-alkoxy, $C$—$C_6$-halogenoalkyl- or $C_1$–$C_6$-halogenoalkoxy-substituted phenoxy-$C_1$–$C_4$-alkyl.

Y preferably represents a direct bond, oxygen, sulphur, carbonyl, carbonyloxy, oxycarbonyl, $C_1$–$C_4$-alkylene, $C_2$–$C_4$-alkenylene, $C_2$–$C_4$-alkenylene, $C_1$–$C_4$-alkyleneoxy, $C_1$–$C_4$-oxyalkylene, $C_1$–$C_4$-thioalkylene, $C_1$–$C_4$-alkylenedioxy or represents p-phenylene which is optionally mono- or disubstituted by radicals from the list $W^1$.

E preferably represents hydrogen, $C_1$–$C_{16}$-alkyl, $C_1$–$C_{16}$-alkenyl, $C_2$–$C_6$-alkinyl, $C_1$–$C_{16}$-halogenoalkyl, $C_2$–$C_{16}$-halogenoalkenyl, optionally halogen-, $C_1$–$C_4$-alkyl-, $C_2$–$C_4$-alkenyl-, $C_2$–$C_4$-halogenoalkenyl-, phenyl-, styryl-, halogenophenyl- or halogenostyryl-substituted $C_3$–$C_8$-cycloalkyl, represents optionally halogen- or $C_1$–$C_4$-alkyl-substituted $C_5$–$C_8$-cycloalkenyl, represents phenyl which is optionally mono- to tetrasubstituted by radicals from the list $W^1$ or represents 5- or 6-membered hetaryl having 1 or 2 hetero atoms from the group consisting of nitrogen, oxygen and sulphur (in particular furyl, thienyl, pyrrolyl, oxazolyl, isoxazolyl, thiazolyl or pyridyl), which is optionally mono- to tetrasubstituted by radicals from the list $W^2$ or represents the grouping

$R^{12}$ preferably represents $C_1$–$C_{12}$-alkyl, $C_1$–$C_{12}$-alkoxy, $C_1$–$C_{12}$-alkenyl, $C_2$–$C_{12}$-alkenyloxy, respectively optionally halogen-, $C_1$–$C_4$-alkyl-, $C_1$–$C_4$-alkenyl-, $C_1$–$C_4$-halogenoalkyl- or $C_2$–$C_4$-halogenoalkenyl-substituted $C_3$–$C_8$-cycloalkyl, $C_3$–$C_8$-cycloalkyloxy or $C_3$–$C_8$-cycloalkyl-$C_1$–$C_6$-alkyloxy or represents phenyl or naphthyl, each of which is optionally mono- to tetrasubstituted by nitro, halogen, $C_1$–$C_{12}$-alkyl, $C_1$–$C_{12}$-alkoxy, $C_1$–$C_{12}$-halogenoalkyl or $C_1$–$C_{12}$-halogenoalkoxy.

$R^{13}$ preferably represents hydrogen or $C_1$–$C_{12}$-alkyl.

$R^{14}$ preferably represents $C_1$–$C_{12}$-alkyl, $C_1$–$C_2$-halogenoalkyl, respectively optionally halogen-, $C_1$–$C_4$-alkyl-, $C_2$–$C_4$-alkenyl-, $C_1$–$C_4$-halogenoalkyl- or $C_2$–$C_4$-halogenoalkenyl-substituted $C_3$–$C_8$-cycloalkyl or $C_3$–$C_8$-cycloalkyl-$C_1$–$C_6$-alkyl, or represents phenyl or phenyl-$C_1$–$C_6$-alkyl which is in each case optionally mono- to tetrasubstituted by halogen, $C_1$–$C_2$-alkyl, $C_1$–$C_{12}$-alkoxy, $C_1$–$C_{12}$-halogenoalkyl or $C_1$–$C_{12}$-halogenoalkoxy.

p, q and r independently of one another each preferably represent 0, 1, 2 or 3, their sum being smaller than 6.

$R^{15}$ and $R^{16}$ independently of one another preferably represent hydrogen or $C_1$–$C_4$-alkyl.

G preferably represents cyano, represents a 5- or 6-membered heterocycle having 1 to 3 identical or different hetero atoms from the group consisting of nitrogen, oxygen and sulphur (in particular 5,6-dihydrodioxazin-2-yl, 3-pyridyl, 3-furyl, 3-thienyl, 2-thiazolyl, 5-thiazolyl, 2-dioxolanyl, 1,3-dioxan-2-yl, 2-dithiolanyl, 1,3-dithian-2-yl or 1,3-thioxan-2-yl), which is optionally mono- to trisubstituted by halogen, $C_1$–$C_4$-alkyl or $C_1$–$C_4$-halogenoalkyl and, at the attachment point, optionally by the radical $R^{17}$, or represents one of the groupings below:

(a)
(b)
(c)
(d)
(e)
(f)
(g)
(h)
(i)
(j)
(k)

$R^{17}$ preferably represents hydrogen, $C_1$–$C_6$-alkyl, $C_2$–$C_6$-alkenyl, $C_1$–$C_4$-halogenoalkyl, $C_2$–$C_6$-halogenoalkenyl, optionally halogen-, $C_1$–$C_4$-alkyl- or $C_1$–$C_4$-halogenoalkyl-substituted $C_3$–$C_6$-cycloalkyl, or represents phenyl which is optionally mono- to pentasubstituted by $C_1$–$C_4$-alkylcarbonylamino, $C_1$–$C_4$-alkylcarbonyl-$C_1$–$C_4$-alkyl amino and/or radicals from the list $W^3$.

$R^{18}$ preferably represents hydrogen, $C_1$–$C_4$-alkyl, $C_2$–$C_6$-alkenyl, $C_1$–$C_4$-halogenoalkyl, $C_2$–$C_6$-halogenoalkenyl, respectively optionally halogen-, $C_1$–$C_4$-alkyl- or $C_1$–$C_4$-halogenoalkyl-substituted $C_3$–$C_6$-cycloalkyl or $C_3$–$C_6$-cycloalkyl-$C_1$–$C_4$-alkyl or represents $C_6$–$C_{10}$-aryl-$C_1$–$C_4$-alkyl which is optionally mono- to tetrasubstituted by radicals from the list $W^3$ (in a particular phenyl-$C_1$–$C_4$-alkyl or naphthyl-$C_1$–$C_4$-alkyl).

$R^{19}$ and $R^{20}$ independently of one another each preferably represent hydrogen, $C_1$–$C_4$-alkyl, $C_3$–$C_6$-alkenyl, $C_1$–$C_4$-halogenoalkyl, $C_3$–$C_6$-halogenoalkenyl, $C_1$–$C_4$-alkoxy, respectively optionally halogen-, $C_1$–$C_4$-alkyl- or $C_1$–$C_4$-halogenoalkyl-substituted $C_3$–$C_6$-cycloalkyl or $C_3$–$C_6$-cycloalkyl-$C_1$–$C_4$-alkyl, represent phenyl or phenyl-$C_1$–$C_4$-alkyl, each of which is optionally mono- to pentasubstituted by radicals from the list $W^3$, represent —$OR^{18}$ or —$NR^{17}R^{18}$ or together represent an alkylene chain having 4 to 6 members in which one methylene group is optionally replaced by oxygen.

$R^{21}$ preferably represents —$OR^{18}$, —$NR^{17}R^{18}$ or —$N(R^{17})$—$COOR^{18}$.

$R^{22}$, $R^{23}$ and $R^{24}$ independently of one another each preferably represent $C_1$–$C_6$-alkyl.

$W^1$ preferably represents hydrogen, halogen, cyano, formyl, nitro, $C_1$–$C_6$-alkyl, tri-$C_1$–$C_4$-alkylsilyl, $C_1$–$C_{16}$-alkoxy, $C_1$–$C_6$-halogenoalkyl, $C_1$–$C_6$-halogenoalkoxy, $C_2$–$C_6$-halogenoalkenyloxy, $C_1$–$C_6$-alkylcarbonyl, $C_1$–$C_{16}$-alkoxycarbonyl, pentafluorothio or —$S(O)_oR^6$ $W^2$ preferably represents halogen, cyano, formyl, nitro, $C_1$–$C_6$-alkyl, tri-$C_1$–$C_4$-alkylsilyl, $C_1$–$C_{16}$-alkoxy, $C_1$–$C_6$-halogenoalkyl, $C_1$–$C_6$-halogenoalkoxy, $C_1$–$C_6$-alkylcarbonyl, $C_1$–$C_6$-alkoxycarbonyl, pentafluorothio, —$S(O)_oR^6$ or —$C(R^{17})$=$N$—$R^{21}$.

$W^3$ preferably represents halogen, cyano, nitro, $C_1$–$C_4$-alkyl, $C_1$–$C_4$-alkoxy, $C_1$–$C_4$-halogenoalkyl, $C_1$–$C_4$-halogenoalkoxy, di-$C_1$–$C_4$-alkylamino, —$S(O)_oR^6$, —$COOR^{25}$ or —$CONR^{26}R^{27}$.

$R^{25}$ preferably represents hydrogen, $C_1$–$C_4$-alkyl, $C_1$–$C_4$-halogenoalkyl, optionally halogen-, $C_1$–$C_4$-alkyl- or $C_1$–$C_4$-halogenoalkyl-substituted $C_3$–$C_7$-cycloalkyl or represents phenyl which is optionally mono- to pentasubstituted by radicals from the list $W^4$.

$R^{26}$ and $R^{27}$ independently of one another each preferably represent hydrogen, $C_1$–$C_4$-alkyl, $C_3$–$C_6$-alkenyl, $C_1$–$C_4$-halogenoalkyl, $C_3$–$C_6$-halogenoalkenyl, $C_1$–$C_4$-alkoxy, respectively optionally halogen-, $C_1$–$C_4$-alkyl- or $C_1$–$C_4$-halogenoalkyl-substituted $C_3$–$C_6$-cycloalkyl or $C_3$–$C_6$-cycloalkyl-$C_1$–$C_4$-alkyl or represent phenyl or phenyl-$C_1$–$C_4$-alkyl, each of which is optionally mono- to pentasubstituted by radicals from the list $W^4$, represent —$OR^{22}$ or —$NR^{23}R^{24}$, or together represent an alkylene chain having 4 to 6 members in which one metlhylene group is optionally replaced by oxygen $W^4$ preferably represents halogen, cyano, nitro, $C_1$–$C_6$-alkyl, $C_1$–$C_6$-alkoxy, $C_1$–$C_6$-halogenoalkyl, $C_1$–$C_6$-halogenoalkoxy, di-$C_1$–$C_4$-alkyl amino, $C_1$–$C_6$-alkoxycarbonyl, di-$C_1$–$C_6$-alkylaminocarbonyl or —$S(O)_o R^6$.

n particularly preferably represents 1 or 2.

$Ar^1$ particularly preferably represents the radical

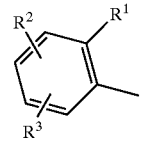

$Ar^2$ particularly preferably represents the radical

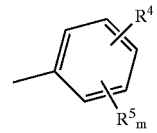

m particularly preferably represents 0, 1 or 2.

$R^1$ particularly preferably represents fluorine, chlorine, bromine, $C_1$–$C_6$-alkyl, $C_1$–$C_6$-alkoxy, respectively fluorine- or chlorine-substituted $C_1$–$C_6$-alkyl or $C_1$–$C_6$-alkoxy, represents $C_1$–$C_6$-alkoxy-$C_1$–$C_6$-alkyl or —$S(O)_o R^6$.

$R^2$ and $R^3$ independently of one another each particularly preferably represent hydrogen, fluorine, chlorine, bromine, iodine, $C_1$–$C_6$-alkyl, $C_1$–$C_6$-alkoxy, respectively fluorine- or chlorine-substituted $C_1$–$C_6$-alkyl or $C_1$–$C_6$-alkoxy, represent $C_1$–$C_6$-alkoxy-$C_1$–$C_6$-alkyl or —$S(O)_oR^6$ $R^4$ particularly preferably represents a substituent in meta- or paraposition from the group consisting of fluorine, chlorine, bromine, iodine, cyano, tri-($C_1$–$C_4$-alkyl)-silyl, —$CO$—$NR^{10}R^{11}$, tetrahydropyranyl or one of the groupings below $$—X—A \qquad (l)$$

$$—B—Z—D \qquad (m)$$

$$—Y—E. \qquad (n)$$

$R^5$ particularly preferably represents hydrogen, fluorine, chlorine, bromine, iodine, cyano, nitro, $C_1$–$C_{16}$-alkyl, $C_1$–$C_{16}$-alkoxy, respectively fluorine- or chlorine-substituted $C_1$–$C_6$-alkyl or $C_1$–$C_6$-alkoxy, represents $C_1$–$C_8$-alkoxy-$C_1$–$C_8$-alkoxy, or —$S(O)_oR^6$.

o particularly preferably represents 0, 1 or 2.

$R^6$ particularly preferable represents $C_1$–$C_4$-alkyl or respectively fluorine- or chlorine-substituted methyl or ethyl.

$R^{10}$ and $R^{11}$ independently of one another each particularly preferably represent hydrogen, $C_1$–$C_6$-alkyl, fluorine- or chlorine-substituted $C_1$–$C_6$-alkyl or represent phenyl or benzyl, each of which is optionally mono- or di-substituted by radicals from the list $W^1$.

X particularly preferably represents a direct bond, oxygen, sulphur, carbonyl, carbonyloxy, oxycarbonyl, $C_1$–$C_4$-alkylene, $C_2$–$C_4$-alkenylene, $C_1$–$C_4$-alkenylene, $C_1$–$C_4$-alkyleneoxy, $C_1$–$C_4$-oxyalkylene, $C_1$–$C_4$-thioalkylene, $C_1$–$C_4$-alkylenedioxy or di-$C_1$–$C_4$-alkylsilylene.

A particularly preferably represents phenyl, naphthyl or tetrahydronaphthyl, each of which is optionally mono- to trisubstituted by radicals from the list $W^1$, or represents a 5- to 10-membered heterocyclyl having 1 to 4 hetero atoms, which includes 0 to 4 nitrogen atoms, 0 to 2 oxygen atoms and 0 to 2 sulphur atoms, and containing 1 or 2 aromatic rings, which is in each case optionally mono- to trisubstituted by radicals from the list $W^2$ (in particular furyl, benzofuryl, thienyl, benzothienyl, oxazolyl, benzoxazolyl, thiazolyl, benzthiazoyl, pyrrolyl, pyridyl, pyrimidyl, 1,3,5-triazinyl, quinolinyl, isoquinolinyl, indolyl, purinyl, benzodioxolyl, indanyl, benzodioxanyl or chromanyl)

B particularly preferably represents p-phenylene which is optionally mono- or disubstituted by radicals from the list $W^1$.

Z particularly preferably represents oxygen or sulphur.

D particularly preferably represents hydrogen, $C_1$–$C_{16}$-alkyl, $C_2$–$C_{16}$-alkenyl, $C_2$–$C_6$-alkinyl, respectively fluorine- or chlorine-substituted $C_1$–$C_4$-alkyl or $C_2$–$C_4$-alkenyl, represents $C_3$–$C_6$-cycloalkyl or $C_3$–$C_6$-cycloalkyl-$C_1$–$C_4$-alkyl, each of which is optionally substituted by fluorine, chlorine, bromine, $C_1$–$C_4$-alkyl, $C_2$–$C_4$-alkenyl, fluorine- or chlorine-substituted $C_2$–$C_4$-alkenyl, phenyl, styryl, respectively fluorine-, chlorine- or bromine-substituted phenyl or styryl, represents respectively optionally fluorine-, chlorine-, bromine- or $C_1$–$C_4$-alkyl-substituted $C_1$–$C_6$-cycloalkenyl or $C_1$–$C_6$-cycloalkenyl-$C_1$–$C_4$-alkyl, represents phenyl-$C_1$–$C_4$-alkyl, naphthyl-$C_1$–$C_4$-alkyl, tetrahydronaphthyl-$C_1$–$C_6$-alkyl or 5- or 6-membered hetaryl-$C_1$–$C_4$-alkyl having 1 or 2 hetero atoms from the group consisting of nitrogen, oxygen and sulphur (in particular furylmethyl, thienylmethyl, pyrrolylmethyl, oxazolylmethyl, isoxazolylmethyl, thioazolylmethyl or pyridylmethyl), each of these radicals being optionally substituted by nitro, fluorine, chlorine, bromine, $C_1$–$C_6$-alkyl, $C_1$–$C_6$-alkoxy, respectively fluorine- or chlorine-substituted $C_1$–$C_4$-alkyl or $C_1$–$C_4$-alkoxy, represents —CO—$R^{12}$, —CO—$NR^{13}R^{14}$ or the grouping

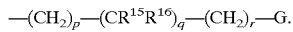
—(CH$_2$)$_p$—(CR$^{15}$R$^{16}$)$_q$—(CH$_2$)$_r$—G.

Z and D also particularly preferably together represent phenoxy-$C_1$–$C_3$-alkyl which is optionally substituted by nitro, fluorine, chlorine, bromine, $C_1$–$C_4$-alkyl, $C_1$–$C_4$-alkoxy or respectively fluorine- or chlorine-substituted $C_1$–$C_4$-alkyl or $C_1$–$C_4$alkoxy.

Y particularly preferably represents a direct bond, oxygen, sulphur, carbonyl, carbonyloxy, oxycarbonyl, $C_1$–$C_4$-alkylene, $C_2$–$C_4$-alkenylene, $C_1$–$C_4$-alkenylene, $C_1$–$C_4$-alkyleneoxy, $C_1$–$C_4$-oxyalkylene, $C_1$–$C_4$-thioalkylene, $C_1$–$C_4$-alkylenedioxy or represents p-phenylene which is optionally mono- or disubstituted by radicals from the list W.

E particularly preferably represents hydrogen, $C_1$–$C_{16}$-alkyl, $C_2$–$C_{16}$-alkenyl, $C_2$–$C_6$-alkinyl, respectively fluorine- or chlorine-substituted $C_1$–$C_4$-alkyl or $C_2$–$C_4$-alkenyl, represents $C_3$–$C_6$-cycloalkyl which is optionally substituted by fluorine, chlorine, bromine, $C_1$–$C_4$-alkyl, $C_2$–$C_4$-alkenyl, fluorine- or chlorine-substituted $C_2$–$C_4$-alkenyl, phenyl, styryl or respectively fluorine-, chlorine- or bromine-substituted phenyl or styryl, represents optionally fluorine-, chlorine-, bromine- or $C_1$–$C_4$-alkyl-substituted $C_5$–$C_6$-cycloalkenyl, represents phenyl which is optionally mono- to trisubstituted by radicals from the list $W^1$ or represents 5- or 6-membered hetaryl having 1 or 2 hetero atoms from the group consisting of nitrogen, oxygen and sulphur (in particular furyl, thienyl, pyrrolyl, oxazolyl, isoxazolyl, thiazolyl or pyridyl), which is optionally mono- or disubstituted by radicals from the list $W^2$, or represents the grouping

—(CH$_2$)$_p$—(CR$^{15}$R$^{16}$)$_q$—(CH$_2$)$_r$—G $R^{12}$ particularly preferably represents $C_1$–$C_6$-alkyl, $C_1$–$C_6$-alkoxy, $C_2$–$C_6$-alkenyl, $C_2$–$C_6$-alkenyloxy, represents $C_3$–$C_6$-cycloalkyl, $C_3$–$C_6$-cycloalkyloxy or $C_3$–$C_6$-cycloalkyl-$C_1$–$C_2$-alkyloxy, each of which is optionally substituted by fluorine, chlorine, $C_1$–$C_3$-alkyl, or respectively fluorine- or chlorine-substituted $C_1$–$C_2$-alkyl or $C_2$–$C_3$-alkenyl, or represents phenyl which is optionally mono- or disubstituted by fluorine, chlorine, bromine, iodine, $C_1$–$C_4$-alkyl, $C_1$–$C_4$-alkoxy or respectively fluorine- or chlorine-substituted $C_1$–$C_3$-alkyl or $C_1$–$C_4$-alkoxy.

$R^{13}$ particularly preferably represents hydrogen or $C_1$–$C_4$-alkyl.

$R^{14}$ particularly preferably represents $C_1$–$C_4$-alkyl, or represents phenyl or benzyl, each of which is optionally mono- or disubstributed by fluorine, chlorine, bromine, $C_1$–$C_4$-alkyl or respectively fluorine- or chlorine-substituted $C_1$–$C_4$-alkyl or $C_1$–$C_4$-alkoxy, p, q and r independently of one another each particularly preferably represent 0, 1, 2 or 3, their sum being smaller than 6

$R^{15}$ and $R^{16}$ independently of one another each particularly preferably represent hydrogen or $C_1$–$C_4$-alkyl.

G particularly preferably represents cyano, represents a 5- or 6-membered heterocycle having 1 to 3 identical or different hetero atoms from the group consisting of nitrogen, oxygen and sulphur (in particular 5,6-dihydrodioxazin-2-yl, 3-pyridyl, 3-furyl, 3-thienyl, 2-triazolyl, 5-thiazolyl, 2-dioxolanyl, 1,3-dioxan-2-yl, 2-dithiolanyl, 1,3-dithian-2-yl or 1,3-thioxan-2-yl), which is optionally mono- to trisubstituted by fluorine, chlorine, bromine, $C_1$–$C_4$-alkyl or fluorine- or chorine-substituted $C_1$–$C_4$-alkyl and, at the attachment point, optionally by the radical $R^{17}$, or represents one of the groupings below:

(a)

(b)

(c)

(d)

(e)

(f)

(g)

(h)

(i)

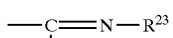(j)

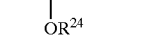(k)

$R^{17}$ particularly preferably represents hydrogen, $C_1$–$C_6$-alkyl, $C_2$–$C_6$-alkenyl, respectively fluorine- or chlorine-substituted $C_1$–$C_4$-alkyl or $C_2$–$C_6$-alkenyl, represents $C_3$–$C_6$-cycloalkyl which is optionally substituted by fluorine, chlorine, $C_1$–$C_4$-alkyl or fluorine- or chlorine-substituted $C_1$–$C_4$-alkyl, or represents phenyl which is optionally mono- to trisubstituted by $C_1$–$C_4$-alkylcarbonylamino, $C_1$–$C_4$-alkylcarbonyl-$C_1$–$C_4$-alkylamino and/or radicals from the list $W^3$.

$R^{18}$ particularly preferably represents hydrogen, $C_1$–$C_4$-alkyl, $C_3$–$C_6$-alkenyl, respectively fluorine- or chlorine-substituted $C_1$–$C_4$-alkyl or $C_3$–$C_6$-alkenyl, represents $C_3$–$C_6$-cycloalkyl or $C_3$–$C_6$-cycloalkyl-$C_1$–$C_4$-alkyl, each of which is optionally substituted by fluorine, chlorine, $C_1$–$C_4$-alkyl or fluorine- or chlorine-substituted $C_1$–$C_4$-alkyl, or represents phenyl-$C_1$–$C_4$-alkyl or naphthyl-$C_1$–$C_4$-alkyl, each of which is optionally mono- to trisubstituted by radicals from the list $W^3$ $R^{19}$ and $R^{20}$ independently of one another each particularly preferably represent hydrogen, $C_1$–$C_4$-alkyl, $C_3$–$C_6$-alkenyl, respectively fluorine- or chlorine-substituted $C_1$–$C_4$-alkyl or $C_3$–$C_6$-alkenyl, represent $C_1$–$C_4$-alkoxy, represent $C_3$–$C_6$-cycloalkyl or $C_3$–$C_6$-cycloalkyl-$C_1$–$C_4$-alkyl, each of which is optionally substituted by fluorine, chlorine, $C_1$–$C_4$-alkyl or fluorine- or chlorine-substituted $C_1$–$C_4$-alkyl, represent phenyl or phenyl-$C_1$–$C_4$-alkyl, each of which is optionally mono- to trisubstituted by radicals from the list $W^3$, represent —$OR^{18}$ or —$NR^{17}R^{18}$ or together represent —$(CH_2)_5$—, —$(CH_2)_6$— or —$(CH_2)_2$—O—$(CH_2)_2$—.

$R^{21}$ particularly preferably represents —$OR^{18}$, —$NR^{17}R^{18}$ or —$N(R^{17})$—$COOR^{18}$ $R^{22}$, $R^{23}$ and $R^{24}$ independently of one another each particularly preferably represent $C_1$–$C_4$-alkyl, $W^1$ particularly preferably represents hydrogen, fluorine, chlorine, bromine, iodine, cyano, formyl, nitro, $C_1$–$C_4$-alkyl, $C_1$–$C_4$-alkoxy, respectively fluorine- or chlorine-substituted $C_1$–$C_4$-alkyl or $C_1$–$C_4$-alkoxy, represents $C_1$–$C_4$-alkylcarbonyl, $C_1$–$C_4$-alkoxycarbonyl or —$S(O)_o$—$R^6$ $W^2$ particularly preferably represents fluorine, chlorine, bromine, cyano, formyl, nitro, $C_1$–$C_4$-alkyl, $C_1$–$C_4$-alkoxy, respectively fluorine- or chlorine-substituted $C_1$–$C_4$-alkyl or $C_1$–$C_4$-alkoxy, represents $C_1$–$C_4$-alkylcarbonyl, $C_1$–$C_4$-alkoxycarbonyl, —$S(O)_o R^6$ or —$C(R^{17})$=N—$R^{21}$.

$W^3$ particularly preferably represents fluorine, chlorine, bromine, cyano, nitro, $C_1$–$C_4$-alkyl, $C_1$–$C_4$-alkoxy, respectively fluorine- or chlorine-substituted $C_1$–$C_4$-alkyl or $C_1$–$C_4$-alkoxy, represents di-$C_1$–$C_4$-alkylamino, —$S(O)_o R^6$, —$COOR^{25}$ or —$CONR^{26}R^{27}$.

$R^{25}$ particularly preferably represents hydrogen, $C_1$–$C_4$-alkyl, fluorine- or chlorine-substituted $C_1$–$C_4$-alkyl, represents $C_3$–$C_6$-cycloalkyl which is optionally substituted by fluorine, chlorine, $C_1$–$C_4$-alkyl or fluorine- or chlorine-substituted $C_1$–$C_4$-alkyl, or represents phenyl which is optionally mono- to trisubstituted by radicals from the list $W^4$.

$R^{26}$ and $R^{27}$ independently of one another each particularly preferably represent hydrogen, $C_1$–$C_4$-alkyl, $C_3$–$C_6$-alkenyl, respectively fluorine- or chlorine-substituted $C_1$–$C_4$-alkyl or $C_3$–$C_6$-alkenyl, represent $C_1$–$C_4$-alkoxy, represent $C_3$–$C_6$-cycloalkyl or $C_3$–$C_6$-cycloalkyl-$C_1$–$C_4$-alkyl, each of which is optionally substituted by fluorine, chlorine, $C_1$–$C_4$-alkyl or fluorine- or chlorine-substituted $C_1$–$C_4$-alkyl, or represent phenyl or phenyl-$C_1$–$C_4$-alkyl, each of which is optionally mono- to trisubstituted by radicals from the list $W^4$, represent —$OR^{22}$ or —$NR^{23}R^{24}$ or together represent —$(CH_2)_5$—, —$(CH_2)_6$— or —$(CH_2)_2$—O—$(CH_2)_2$ $W^4$ particularly preferably represents fluorine, chlorine, bromine, cyano, nitro, $C_1$–$C_4$-alkyl, $C_1$–$C_4$-alkoxy, respectively fluorine- or chlorine-substituted $C_1$–$C_4$-alkyl or $C_1$–$C_4$-alkoxy, di-$C_1$–$C_4$-alkylamino, $C_1$–$C_4$-alkoxycarbonyl, di-$C_1$–$C_6$-alkylaminocarbonyl or —$S(O)_o R^6$ n very particularly preferably represents 1 or 2, especially represents I $Ar^1$ very particularly preferably represents the radical

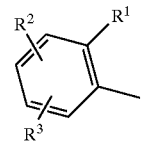

$Ar^2$ very particularly preferably represents the radical

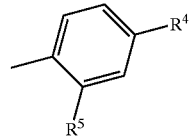

$R^1$ very particularly preferably represents fluorine, chlorine, bromine, methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy.

$R^2$ and $R^3$ independently of one another each very particularly preferably represent hydrogen, fluorine, chlorine, bromine, methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy.

$R^4$ very particularly preferably represents a substituent in meta- or paraposition from the group consisting of fluorine, chlorine, bromine, iodine, cyano, —CO—$NR^{10}R^{11}$, tetrahydropyranyl or one of the groupings below

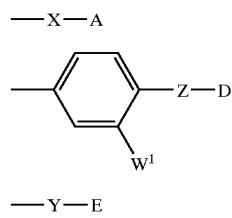

$R^5$ very particularly preferably represents hydrogen, fluorine, Chlorine, bromine, methyl, ethyl, methoxy, ethoxy, methylthio, ethylthio, trifluoromethyl, difluoromethoxy, trifluoromethoxy or trifluoromethylthio o very particularly preferably represents 0 or 2.

$R^6$ preferably represents methyl, ethyl, n-propyl, isopropyl, difluoromethyl or trifluoromethyl.

$R^{10}$ and $R^{11}$ independently of one another each very particularly preferably represent hydrogen, methyl, ethyl, n-propyl, isopropyl, n-butyl, isobutyl, sec-butyl, tert-butyl or represent phenyl or benzyl, each of which is optionally monosubstituted by a radical from the list $W^1$.

X very particularly preferably represents a direct bond, oxygen, sulphur, carbonyl, —CH$_2$—, —(CH$_2$)$_2$—, —CH=CH— (E or Z), —C≡C—, —CH$_2$O—, —(CH$_2$)$_2$ O—, —CH(CH$_3$)O—, —OCH$_2$—, —O(CH$_2$)$_2$—, —SCH$_2$—, —S(CH$_2$)$_2$—, —SCH(CH$_3$)—, $C_1$-$C_4$-alkylenedioxy, in particular —OCH$_2$O—, —O(CH$_2$)$_2$ O— or —OCH(CH$_3$)O—.

A very particularly preferably represents phenyl which is optionally mono- or disubstituted by radicals from the list $W^1$ or represents furyl, benzofuryl, thienyl, benzothienyl, oxazolyl, benzoxazolyl, thiazolyl, benzthiazolyl, pyrrolyl, pyridyl, pyrimidyl, 1,3,5-triazinyl, quinolinyl, isoquinolinyl, indolyl, purinyl, benzodioxolyl, indanyl, benzodioxanyl or chromanyl, each of which is optionally mono- or disubstituted by radicals from the list $W^2$.

Z very particularly preferably represents oxygen or sulphur.

D very particularly preferably represents hydrogen, methyl, ethyl, n-propyl, isopropyl, n-butyl, isobutyl, sec-butyl, tert-butyl, the isomeric pentyls, the isomeric hexyls, n-heptyl, n-octyl, n-isooctyl, n-nonyl, n-decyl, n-undecyl, n-dodecyl, n-tridecyl, n-tetradecyl, n-pentadecyl, n-hexadecyl, 2-propenyl, butenyl, pentenyl, hexenyl, propargyl, butinyl, pentinyl, —CF$_3$, —CHF$_2$, —CClF$_2$, —CF$_2$CHFCl, —CF$_2$CH$_2$F, —CF$_2$CHF$_2$, —CF$_2$CCl$_3$, —CH$_2$CF$_3$, —CF$_2$CHFCF$_3$, —CH$_2$CF$_2$CHF$_2$, —CH$_2$CF$_2$CF$_3$, represents cyclopropyl, cyclobutyl, cyclopentyl, cyclohexyl, cyclopropylmethyl, cyclobutylmethyl, cyclopentylmethyl or cyclohexylmethyl, each of which is optionally mono- to trisubstituted by fluorine, chlorine, bromine, methyl, ethyl, n-propyl, isopropyl, n-butyl, isobutyl, sec-butyl, tert-butyl, ethenyl, 1-propenyl, 2,2-dimethylethenyl, —CH=CCl$_2$, phenyl, styryl, respectively fluorine-, chlorine- or bromine-substituted phenyl or 4-chlorostyryl, represents respectively optionally fluorine-, chlorine-, methyl-, ethyl-, n-propyl-, iso-propyl-, n-butyl-, isobutyl-, sec-butyl- or tert-butyl-substituted cyclopentenyl, cyclohexenyl, cyclohexenylmethyl or cyclopentenylmethyl, represents benzyl, phenethyl, naphthylmethyl, tetrahydronaphthylmethyl, furylmethyl, thienylmethyl, pyrrolylmethyl, oxazolylmethyl, isoxazolylmethyl, thiazolylmethyl or pyridylmethyl, each of which is optionally mono- or disubstituted by nitro, fluorine, chlorine, bromine, methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy, trifluoromethyl, trifluoromethoxy, difluoromethoxy or chlorodifluoromethoxy, represents —CO—$R^{12}$, —CO—NR$^{13}$R$^{14}$ or the grouping —(CH$_2$)$_p$—(CR$^{15}$R$^{16}$)$_q$—(CH$_2$)$_r$—G.

Z and D also very particularly preferably together represent phenoxymethyl which is optionally mono- or disubstituted by nitro, fluorine, chlorine, bromine, methyl, ethyl, n-propyl, isopropyl, methoxy, ethoxy, n-propoxy, isopropoxy, trifluoromethyl, trifluoromethoxy, difluoromethoxy or chlorodifluoromethoxy.

Y very particularly preferably represents a direct bond, oxygen, sulphur, carbonyl, —CH$_2$—, —(CH$_2$)$_2$—, —CH—CH— (E or Z), —C≡C—, —CH$_2$O—, —(CH$_2$)$_2$ O—, —CH(CH$_3$)O—, —OCH$_2$—, —O(CH$_2$)$_2$—, —SCH$_2$—, —S(CH$_2$)$_2$—, —SCH(CH$_3$)—, $C_1$-$C_4$-alkylenedioxy, in particular —OCH$_2$O— or —O(CH$_2$)$_2$ O— or represents p-phenylene which is optionally monosubstituted by a radical from the list $W^1$.

E very particularly preferably represents hydrogen, methyl, ethyl, n-propyl, isopropyl, n-butyl, isobutyl, sec-butyl, tert-butyl, the isomeric pentyls, the isomeric hexyls, n-heptyl, n-octyl, n-isooctyl, n-nonyl, n-decyl, n-undecyl, n-dodecyl, n-tridecyl, n-tetradecyl, n-pentadecyl, n-hexadecyl, 2-propenyl, butenyl, pentenyl, hexenyl, propargyl, butinyl, pentinyl, —CF$_3$, —CHF$_2$, —CClF$_2$, —CF$_2$CHFCl, —CF$_2$CH$_2$F, —CF$_2$CHF$_2$, —CF$_2$CCl$_3$, —CH$_2$CF$_3$, —CF$_2$CHFCF$_3$, —CH$_2$CF$_2$CHF$_2$, —CH$_2$CF$_2$CF$_3$, represents cyclopropyl, cyclobutyl, cyclopentyl or cyclohexyl, each of which is optionally mono- to tri-substituted by fluorine, chlorine, bromine, methyl, ethyl, n-propyl, iso-propyl, n-butyl, isobutyl, sec-butyl, tert-butyl, ethenyl, 1-propenyl, 2,2-dimethylethenyl, —CH=CCl$_2$, phenyl, styryl, respectively fluorine-, chlorine- or bromine-substituted phenyl or by 4-chlorostyryl, represents respectively optionally fluorine-, chlorine-, methyl-, ethyl-, n-propyl-, isopropyl-, n-butyl-, isobutyl-, sec-butyl- or tert-butyl-substituted cyclopentenyl or cyclohexenyl, represents phenyl which is optionally mono- or disubstituted by radicals from the list $W^1$, represents furyl, thienyl, pyrrolyl, oxazolyl, isoxazolyl, thiazolyl or pyridyl, each of which is optionally mono- or disubstituted by radicals from the list $W^2$, or represents the grouping —(CH$_2$)$_p$—(CR$^{15}$R$^{16}$)$_q$—(CH$_2$)$_r$—G.

$R^{12}$ very particularly preferably represents methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy, cyclopropyl, cyclohexyl, cyclohexyloxy, cyclohexylmethyloxy, phenyl, 2-chlorophenyl, 3-chlorophenyl, 2,6-difluorophenyl, 2,4-dichlorophenyl, 3,4-dichlorophenyl, 2-trifluoromethoxyphenyl or 4-trifluoromethoxyphenyl.

$R^{13}$ very particularly preferably represents hydrogen.

$R^{14}$ very particularly preferably represents methyl, ethyl or represents phenyl which is optionally monosubstituted by chlorine.

p, q and r independently of one another each very particularly preferably represent 0, 1, 2 or 3, their sum being smaller than 4

$R^{15}$ and $R^{16}$ independently of one another each very particularly preferably represent hydrogen, methyl, ethyl, n-propyl, isopropyl, n-butyl, isobutyl, sec-butyl, tert-butyl.

G very particularly preferably represents cyano, represents 5,6-dihydro-dioxazin-2-yl, 3-pyridyl, 3-furyl, 3-thienyl, 2-thiazolyl, 5-thiazolyl, 2-dioxolanyl, 1,3-dioxan-2-yl, 2-dithiolanyl, 1,3-dithian-2-yl or 1,3-thioxan-2-yl, each of which is optionally mono- to trisubstituted by fluorine, chlorine, bromine, methyl, ethyl, n-propyl, isopropyl or trifluoromethyl and, at the attachment point, optionally by the radical $R^{17}$, or represents one of the groupings below:

—CO—$R^{17}$ (a)

—CO—OR$^{18}$ (b)

-continued

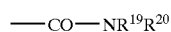  (c)

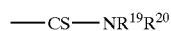  (d)

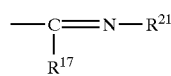  (e)

(f)
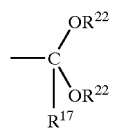

(g)
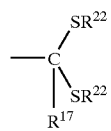

(h)
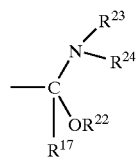

(i)
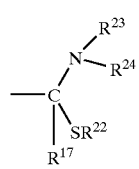

$R^{17}$ very particularly preferably represents hydrogen, methyl, ethyl, n-propyl, isopropyl, n-butyl, isobutyl, sec-butyl, tert-butyl, the isomeric pentyls, the isomeric hexyls, —CF$_3$, —CHF$_2$, —CClF$_2$, —CF$_2$CHFCl, —CF$_2$CH$_2$F, —CF$_2$CHF$_2$, —CF$_2$CCl$_3$, —CH$_2$CF$_3$, C$_3$-C$_6$-alkenyl, C$_3$-C$_6$-alkenyl which is mono- to trisubstituted by fluorine or chlorine, represents cyclopropyl, cyclopentyl or cyclohexyl, each of which is optionally mono- or disubstituted by fluorine, chlorine, methyl, ethyl, n-propyl, isopropyl, —CF$_3$, —CHF$_2$, —CClF$_2$, —CF$_2$CHFCl, —CF$_2$CH$_2$F, —CF$_2$CHF$_2$, —CF$_2$CCl$_3$ or —CH$_2$CF$_3$, or represents phenyl which is optionally mono- or disubstituted by methylcarbonylamino, ethylcarbonylamino, methylcarbonyl-methylamino and/or radicals from the list W$^3$.

$R^{18}$ very particularly preferably represents hydrogen, methyl, ethyl, n-propyl, isopropyl, n-butyl, isobutyl, sec-butyl, tert-butyl, —CH$_2$CF$_3$, allyl, represents cyclopropyl, cyclopentyl, cyclohexyl, cyclopropylmethyl, cyclopentylmethyl, cyclohexylmethyl, cyclopropylethyl, cyclopentylethyl or cyclohexylethyl, each of which is optionally mono- or disubstituted by fluorine, chlorine, methyl, ethyl, n-propyl, isopropyl, —CF$_3$, —CHF$_2$, —CClF$_2$, —CF$_2$CHFCl, —CF$_2$CH$_2$F, —CF$_2$CHF$_2$, —CF$_2$CCl3 or —CH$_2$CF$_3$, or represents benzyl or phenethyl, each of which is optionally mono- or disubstituted by radicals from the list W$^3$.

$R^{19}$ and $R^{20}$ independently of one another each very particularly preferably represent hydrogen, methyl, ethyl, n-propyl, isopropyl, n-butyl, isobutyl, sec-butyl, tert-butyl, —CH$_2$CF$_3$, methoxy, ethoxy, allyl, represent cyclopropyl, cyclopentyl, cyclohexyl, cyclopropylmethyl, cyclopentylmethyl or cyclohexylmethyl, each of which is optionally mono- or disubstituted by fluorine, chlorine, methyl, ethyl, n-propyl, isopropyl or trifluoromethyl, represent phenyl, benzyl or phenethyl, each of which is optionally mono- or disubstituted by radicals from the list W$^3$, represent ~OR$^{18}$ or —NR$^{17}$R$^{18}$ R$^{21}$ very particularly preferably represents —OR$^{18}$, —NR$^{17}$R$^{18}$ or —N(R$^{17}$)—COOR$^{18}$.

$R^{22}$, $R^{23}$ and $R^{24}$ independently of one another each very particularly preferably represent methyl, ethyl, n-propyl or isopropyl W$^1$ very particularly preferably represents hydrogen, fluorine, chlorine, bromine, cyano, formyl, nitro, methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy, —CF$_3$, —CHF$_2$, —CClF$_2$, —CF$_2$CHFCl, —CF$_2$CH$_2$F, —CF$_2$CHF$_2$, —CF$_2$CCl$_3$, —CH$_2$CF$_3$, —CF$_2$CHFCF$_3$, —CH$_2$CF$_2$CHF$_2$, —CH$_2$CF$_2$CF$_3$, trifluoromethoxy, difluoromethoxy, chlorodifluoromethoxy, acetyl, propionyl, butyryl, isobutyryl, methoxycarbonyl, ethoxycarbonyl, n-propoxycarbonyl, isopropoxycarbonyl, n-butoxycarbolyl, isobutoxycarbonyl, sec-butoxycarbonyl, tert-butoxycarbonyl or —S(O)$_o$R$^6$ W$^2$ very particularly preferably represents fluorine, chlorine, bromine, cyano, methyl, ethyl, n-propyl, isopropyl, trifluoromethyl, trifluoromethoxy, difluoromethoxy, chlorodifluoromethoxy, acetyl, trifluoromethylthio or —CH=N—OCH$_3$, —CH=N—OC$_2$H$_5$, —CH=N—OC$_3$H$_7$, —C(CH$_3$)=N—OCH$_3$, —C(CH$_3$)=N—OC$_2$H$_5$, —C(CH$_3$)=N—OC$_3$H$_7$, —C(C$_2$H$_5$)=N—OCH$_3$, —C(C$_2$H$_5$)=N—OC$_2$H$_5$ or —C(C$_2$H$_5$)=N—OC$_3$H$_7$.

W$^3$ very particularly preferably represents fluorine, chlorine, cyano, nitro, methyl, ethyl, methoxy, ethoxy, methylthio, trifluoromethyl, trifluoromethoxy, trifluoromethylthio, dimethylamino, diethylamino, —COOR$^{25}$ or CONR26R$^{27}$.

$R^{25}$ very particularly preferably represents hydrogen, methyl, ethyl, n-propyl, isopropyl, tert-butyl, —CH$_2$CF$_3$, represents cyclopropyl, cyclopentyl or cyclohexyl, each of which is optionally mono- or disubstituted by fluorine, chlorine, methyl, ethyl, n-propyl, isopropyl or —CF$_3$, or represents phenyl which is optionally mono- or disubstituted by radicals from the list W$^4$.

$R^{26}$ and $R^{27}$ independently of one another each very particularly preferably represent hydrogen, methyl, ethyl, n-propyl, isopropyl, n-butyl, isobutyl, sec-butyl, tert-butyl, —CH$_2$CF$_3$, methoxy, ethoxy, allyl, represent cyclopropyl, cyclopentyl, cyclohexyl, cyclopropylmethyl, cyclopentylmethyl or cyclohexylmethyl, each of which is optionally mono- or disubstituted by fluorine or chlorine, represent phenyl, benzyl or phenethyl, each of which is optionally mono- or disubstituted by radicals from the list W$^4$, represent —OR$^{22}$ or NR$^{23}$R$^{24}$.

W$^4$ very particularly preferably represents fluorine, chlorine, bromine, cyano, nitro, methyl, ethyl, tert-butyl, methoxy, ethoxy, methylthio, trifluoromethyl, trifluoromethoxy or trifluoromethylthio.

Furthermore, preference is given to compounds of the formula (I-a)

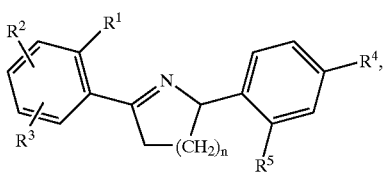

in which
R$^1$, R$^2$, R$^3$, R$^5$ and n each have the abovementioned general, preferred, particularly preferred or very particularly preferred meanings,
R$^4$ represents phenyl which is mono- or disubstituted by radicals from the list W$^1$ or one of the groupings below —B—O—D     (m-b)

—Y—E,     (l)

B represents p-phenylene which is optionally monosubstituted by a radical from the list W$^1$,
Y represents a direct bond or represents p-phenylene which is optionally mono- or disubstituted by radicals from the list W$^1$ and
D and E each have the abovementioned very particularly preferred meanings where
  G represents cyano or one of the groupings below

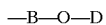     (a)

     (e)

in which
R$^{17}$ and R$^{21}$ each have the abovementioned general, preferred, particularly or very particularly preferred meanings and
W$^1$ has the abovementioned general, preferred, particularly preferred or very particularly preferred meaning.

Furthermore, preference is given to compounds of the formula (I-f)

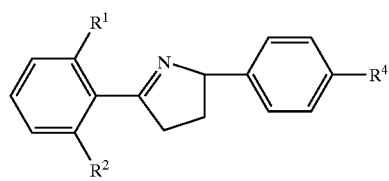

in which
R$^1$ represents halogen, in particular fluorine or chlorine, especially fluorine,
R$^2$ represents halogen, in particular fluorine or chlorine, especially fluorine and
R$^4$ represents
  a) phenyl which is mono- or disubstituted by radicals from the list W$^2$ or
  b) hetaryl (in particular furyl, thienyl, pyrrolyl, oxazolyl, isoxazolyl, thiazolyl or pyridyl, especially thienyl) which is mono or disubstituted by radicals from the list W$^2$.

The abovementioned general or preferred definitions of radicals or illustrations can be combined with each other as desired, that is to say combinations between the respective ranges and preferred ranges are also possible. The definitions apply to the end products and, correspondingly, to the precursors and intermediates.

Preference according to the invention is given to compounds of the formula (I) which contain a combination of the definitions given above as being preferred (preferably).

Particular preference according to the invention is given to compounds of the formula (I) which contain a combination of the definitions given above as being particularly preferred.

Very particular preference according to the invention is given to compounds of the formula (I) which contain a combination of the definitions given above as being, very particularly preferred.

Saturated or unsaturated hydrocarbon radicals such as alkyl or alkenyl may be—also in connection with hetero atoms such as, for example, in alkoxy—in each case straight-chain or branched as far as this is possible.

Optionally substituted radicals may be mono- or polysubstituted, the substituents in the case of polysubstitution being identical or different. If several radicals have identical indices, such as, for example, m radicals R$^5$ in the case m>1, these radicals may be identical or different.

If, for example, [1-(4-ethyl-2-methyl-phenyl)-5-(2-methylbenzoyl)-1-pentyl]-ammonium trifluoroacetate is employed as starting material, the course of the reaction of process (A) according to the invention may be illustrated by the following scheme:

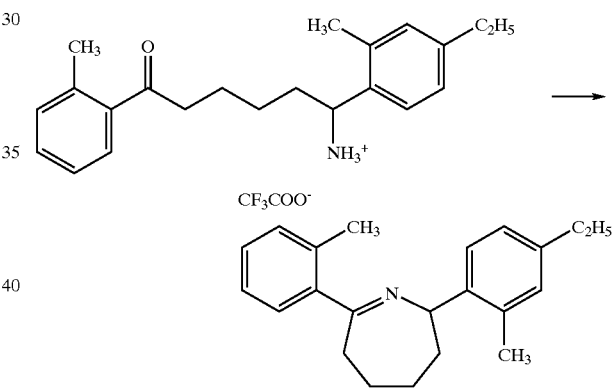

If, for example, 2-(4-methoxyphenyl)-cyclopentanone O-methanesulphonyl oxime and 2-tolylmagnesium bromide are employed as starting materials, the course of the reaction of process (B) according to the invention may be illustrated by the following scheme:

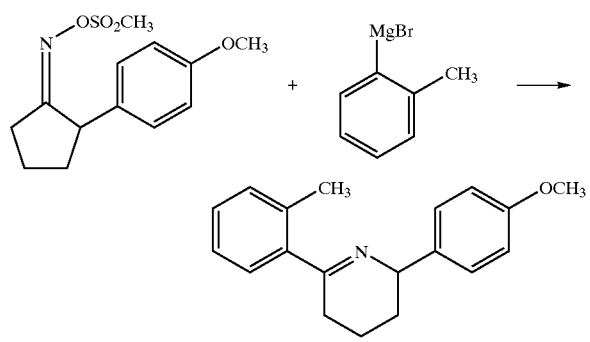

If, for example, 2-(2-methylphenyl)-5-(4-iodophenyl)-3,4-dihydro-2H-pyrrole and 4-cyanomethoxyphenylboronic acid are employed as starting materials, the course of the reaction of process (C) according to the invention may be illustrated by the following scheme:

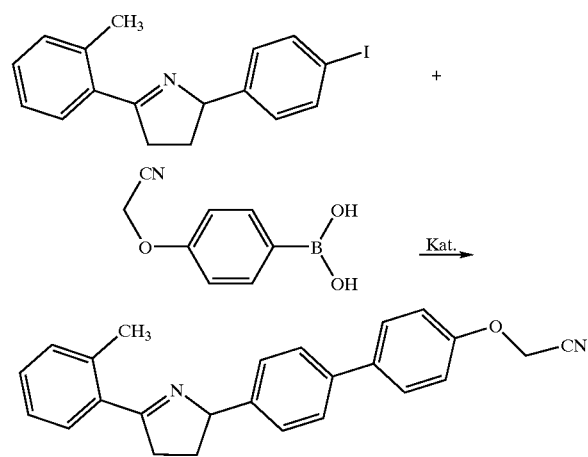

If, for example, 2-(2-bromo-4-fluoro-6-methyl-phenyl)-5-(3'-chloro-4'-hydroxybiphenyl-4-yl)-3,4-dihydro-2H-pyrrole and methyl α-bromovalerate are employed as starting materials, the course of the reaction of process (D) according to the invention may be illustrated by the following scheme:

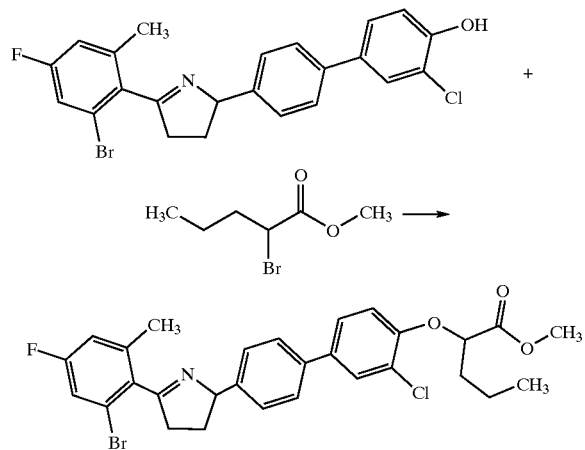

If, for example, 6-(4'-cyclopropylcarbonylmethoxy-3-trifluoromethoxy-biphenyl-4-yl)-(2-methylphenyl)-3,4,5,6,-tetrahydropyridine and O-methyl hydroxylamine are employed as starting materials, the course of the reaction of process (E) according to the invention may be illustrated by the following scheme:

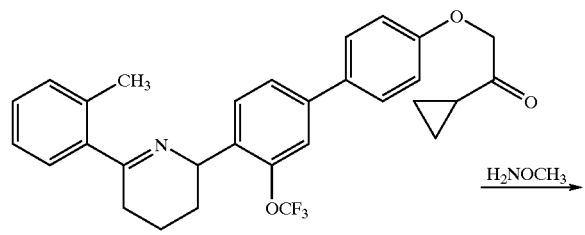

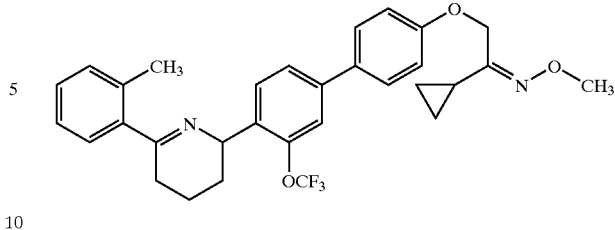

The aminoketones required for carrying out process (A) according to the invention are defined in a general way by the formula (II). In this formula, $Ar^1$, $Ar^2$ and n each preferably have those meanings already mentioned in connection with the description of the cyclic imines of the formula (I) as preferred. The aminoketones of the formula (II) are novel.

Aminoketones of the formula (II) can be prepared, for example, by detaching the BOC (tert-butoxycarbonyl) protecting group of the aminoketone derivatives of the formula (VIII) which are also new in a process (A a) according to the scheme below:

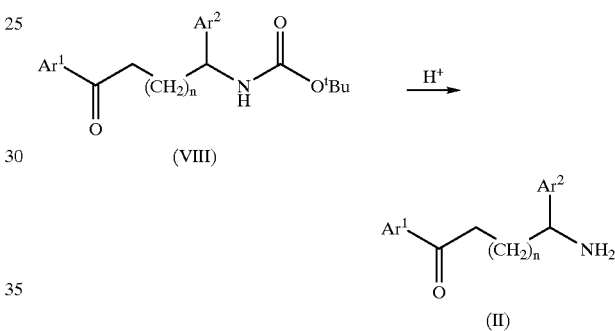

The reaction can be carried out, if appropriate, in the presence of a solvent such as, for example, dichloromethane by means of conventional methods for detaching a tert-butyoxycarbonyl amino protecting group, preferably by acidolysis using trifluoroacetic acid (cf. for example T. W. Greene, P G M Wuts, Protective Groups in Organic Synthesis, 2nd Ed., John Wiley & Sons, New York 1991) Here, the aminoketones of the formula (II) are preferably isolated as salts of an organic or inorganic Bronstedt acid, such as, for example, hydrogen fluoride, hydrogen chloride, sulphuric acid, phosphoric acid, formic acid, acetic acid, benzoic acid, citric acid, trifluoroacetic acid, methanesulphonic acid, trifluoromethanesulphonic acid or toluenesulphonic acid Aminoketone derivatives of the formula (VIII) can be prepared for example by reacting BOC-protected lactams of the formula (IX) with metalated aromatics of the formula (X) at temperatures between 0° C. and 80° C. according to the following scheme:

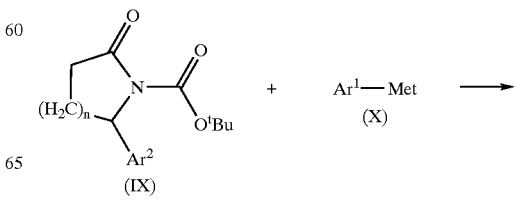

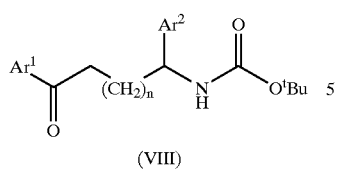

(VIII)

In the formula (X), Met represents a monovalent metal radical such as Li, MgI, MgBr or MgCl.

Some of the metalated aromatics of the formula (X) are known, or they can be prepared by known methods such as, for example, lithiation or Grignard reaction, from the corresponding aromatics or halogenoaromatics.

Protected lactams of the formula (IX) are obtained, for example, by BOC-protecting lactams of the formula (XI) by conventional methods such as, for example, metalation with butyllithium and reaction with di-tert-butyl dicarbonate (cf. for example T. W. Greene, P.G.M. Wuts, Protective Groups in Organic Synthesis, 2nd Ed., John Wiley & Sons, New York 1991).

Lactams of the formula (XI) can be prepared, for example, starting from ω-alkoxylactams of the formula (XII) by two methods. They can be reacted with aromatics of the formula (XIII) in the presence of an acid catalyst, such as, for example, sulphuric acid, acetic acid or aluminium chloride, and optionally in the presence of a diluent, such as, for example, dichloromethane or acetonitrile, according to the following scheme:

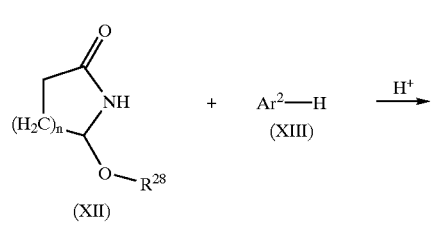

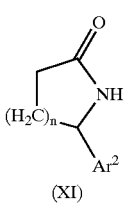

(XI)

Alternatively, they can be reacted with aryl Grignard compounds of the formula (XIV) in the presence of a diluent, such as, for example, tetrahydrofuran, according to the following scheme [cf. Org. Prep. Proced. Int. 25, 255 (1993)]:

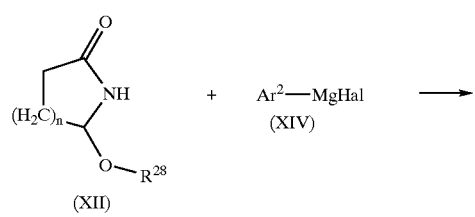

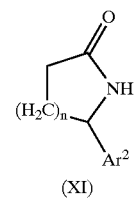

(XI)

In the formula (XII) $R^{28}$ represents methyl or ethyl. In the formula (XIV), Hal represents chlorine, bromine or iodine.

The ω-alkoxylactams of the formula (XII) are known and some of them are commercially available. They can be prepared for example from the corresponding unsubstituted imides by cathodic or sodium boranate reduction or from the unsubstituted lactams by anodic oxidation, in each case in the presence of methanol or ethanol (cf. for example J. Org Chem. 56, 1822 (1991), Synthesis 1980, 315).

The aromatics of the formula (XIII) are benzene derivatives which are generally known or which can be prepared by employing a wide variety of generally known methods of organic chemistry.

The aryl Grignard compounds of the formula (XIV) can be prepared in a conventional manner from the corresponding aryl halides and magnesium. Aryl halides are generally known compounds of organic chemistry.

Lactams of the formula (XI) can also be prepared for example by cyclizing substituted ω-benzoylcarboxylic acids of the formula (XV) with a reagent prepared from ammonium carbonate and formic acid at boiling point according to the following scheme [cf. Recl. Trav. Chim. Bays-Bas 81, 788 (1962)]:

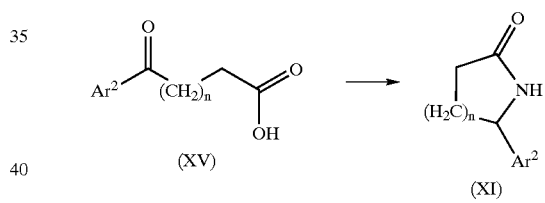

The ω-benzoylcarboxylic acids of the formula (XV) required here can be prepared for example by reacting the dicarboxylic anhydrides of the formula (XVI) with aromatics of the formula (XIII) in the presence of a Lewis acid such as, for example, aluminium chloride and, if appropriate, in the presence of a diluent such as, for example, benzene, according to the following scheme [cf. Recl. Trav. Chim. Bays-Bas 81, 788 (1962)]:

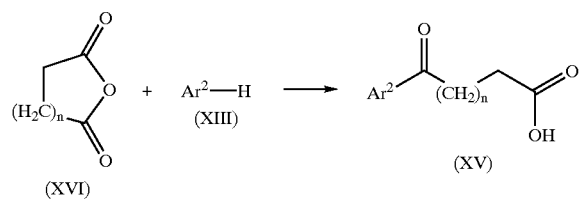

The anhydrides required here are (succinic and glutaric anhydride) or were (adipic anhydride) commercially available [for the preparation of adipic anhydride cf for example Chem. Ber. 120, 285 (1987)].

If $Ar^2$ in the active compound of the formula (I) according to the invention represents an optionally substituted biphenylyl such as in the formula (I-b) shown further above, the corresponding biphenyllactams of the formula (XI-a) can be prepared in an advantageous variant of the process described here by reacting, by the method of the process (C) described above and further below, certain phenyllactams of the formula (XVII) with boronic acids of the formula (VI) according to the following scheme:

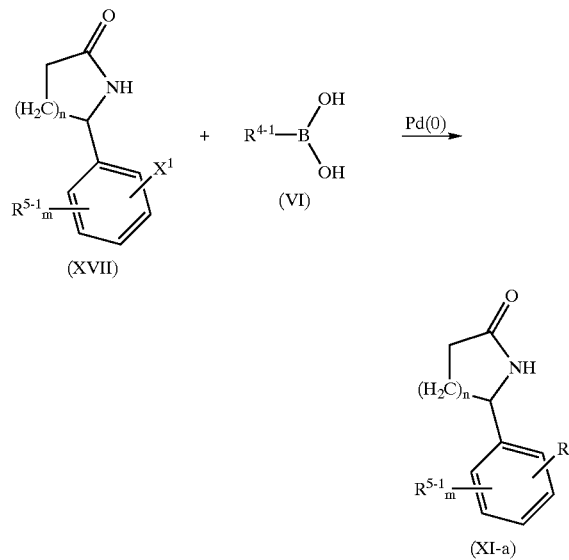

The phenyllactams of the formula (XVII) in which $X^1$ represents bromine or iodine are a subset of the compounds of the formula (XI) whose preparation is described above. The phenyllactams of the formula (XVII) in which $X^1$ represents trifluoromethanesulphonyl can be prepared by the method of process (C) from the corresponding compounds of the formula (XI) in which Ar is substituted by $R^4$=hydroxyl.

The novel aminoketones of the formula (II) can also be prepared, for example, by reducing the nitro group of the nitroketones of the formula (XVIII) which are also novel in a process (A.b) according to the following scheme:

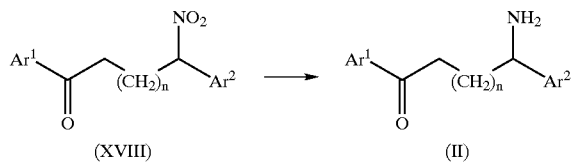

The reduction can be carried out by catalytic hydrogenation or other generally known methods for reducing nitro groups (cf. for example Houben-Weyl, Methoden der Organischen Chemie, Georg Thieme Verlagi Stuttgart, Volume 11/1, 394–409 and Volume 4/1c, 490–506) Preference is given to the methods where the reaction is carried out in acid medium, since the aminoketones of the formula (II) are preferably isolated as salts.

Nitroketones of the forumula (XVIII) can be prepared for example by condensing ω-chloroalkylphenylketones of the formula (XXI) in the presence of a diluent such as, for example, methanol, ethanol, another lower aliphatic alcohol or tetrahydrofuran and in the presence of an acid binding agent such as, for example, sodium hydride or an alkali metal alkoxide, preferably of the corresponding alcohol employed as diluent, according to the scheme below:

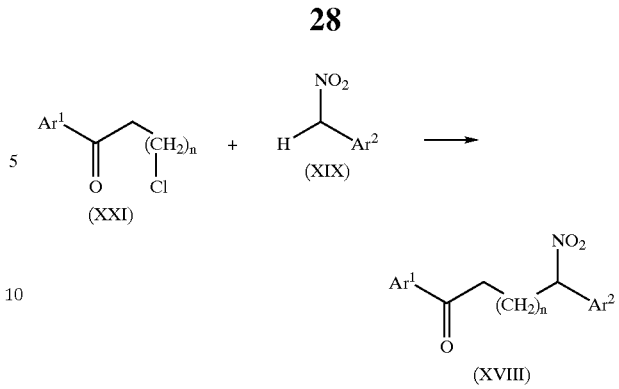

The ω-chloroalkylphenylketones of the formula (XXI) are commercially available, known or can be prepared by employing known methods, for example by Friedel-Crafts-acylation of corresponding benzene derivatives of the formula (XXII) (see below) with 3-chloropropionyl chloride, 4-chlorobutyryl chloride or 5-chloro-pentanoic acid chloride.

The nitromethylbenzenes of the formula (XIX) are known or can be prepared in a known manner, such as, for example, by nitration of the corresponding toluenes in the side chain or reaction of the corresponding benzyl halides with silver nitrite [cf. for example J. Am. Chem. Soc. 77, 6269 (1955); J. Am. Chem. Soc. 86, 2681 (1964); Houben-Weyl, Methoden der Organischen Chemie, Georg Tlieme Verlag Stuttgart, Volume 10/1, 46–57 (halogen substitution), Volume E16, 145–154 (both methods)]. The toluenes or benzyl halides required are generally known compounds of organic chemistry.

The nitroketones of the formula (XVIII) in which n equals 1 (XVIII-a) can be prepared for example by Michael addition of nitrometlhylbenzenes of the formula (XIX) to phenyl vinyl ketones of the formula (XX) in the presence of a diluent such as, for example, methanol, ethanol or another lower aliphatic alcohol and in the presence of an acid binder such as, for example, preferably an alkali metal alkoxide of the corresponding alcohol employed as diluent, according to the scheme below (cf. for example J. Prakt. Chem., Series 4, 1, 57 (1955), Flouben-Weyl, Methoden der Organischen Chemie, Georg Thieme VerlagY Stuttgart, Volume 10/1, 199–206):

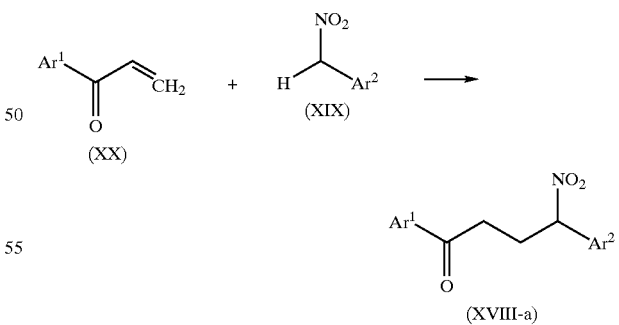

The phenyl vinyl ketones of the formula (XX) can be prepared for example by eliminating hydrogen chloride from β-chloropropiophenones of the formula (XXI-a) which are obtainable for example by Friedel-Crafts acylation of the corresponding benzene derivatives of the formula (XXII) with 3-chloropropionyl chloride, in the presence of an acid binder such as, for example, potassium acetate and in the presence of a diluent such as, for example, methanol, according to the following scheme [cf. for example J. Prakt. Chem., Series 4, 1, 57 (1955)]:

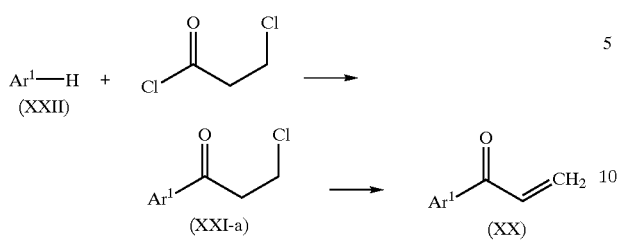

Some of the benzene derivatives of the formula (XXII) are commercially available or known, or they can be prepared by generally known methods of the chemistry of aromatics.

The phenyl vinyl ketones of the formula (XX) can also be prepared by reacting O-methyl methylbenzohydroxamates of the formula (XXIII) with vinylmagnesium bromide according to the following scheme:

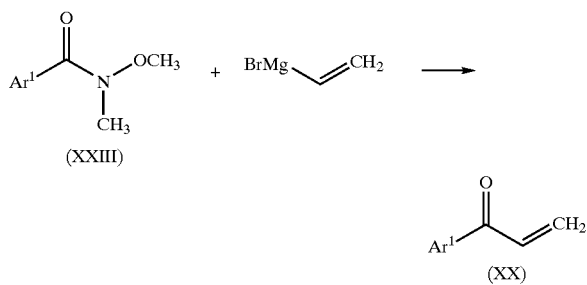

Some of the O-methyl methylbenzohydroxamates of the formula (XXIII) are known ("Weinreb amides"), or they can be prepared by known methods, for example from the corresponding benzoic acid derivatives [cf. for example Tetrahedron Lett. 22, 3815 (1981)].

Since some of the phenyl vinyl ketones of the formula (XX) are unstable they are, in a preferred variant for preparing the nitroketones of the formula (XVIII-a), directly reacted with nitromethylbenzenes of the formula (XIX).

Nitroketones of the formula (XVIII-a) can also be prepared by adding enamines of methyl phenyl ketones of the formula (XXVI) to (x-nitrostyrenes of the formula (XXVII) and hydrolyzing the reaction product under acidic conditions according to the following scheme:

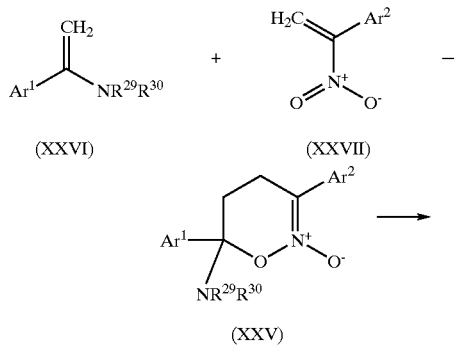

-continued

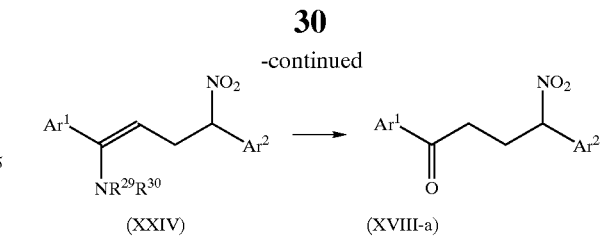

In the formulae (XXIV), (XXV) and (XXVI), $R^{29}$ and $R^{30}$ together with the nitrogen atom to which they are attached represent a cyclic amino radical such as, for example, I-pyrrolidino, I-piperidino or 4-morpholino.

In most instances, the addition proceeds in a [4+2]-cycloaddition to afford 1,2-oxazine N-oxide derivatives of the formula (XXV) which can be isolated, and the reaction is, if appropriate, carried out in the presence of an apolar diluent such as, for example, diethyl ether, at, for example, −80° to +20° C. The hydrolysis is carried out using for example aqueous mineral acids such as hydrochloric acid, if appropriate in the presence of methanol or ethanol [cf. for example Helv Chim Acta 68, 162 (1985); Tetrahedron 45, 2099 (1989)]. In many instances it is advantageous first to open the ring to afford compounds of the formula (XXIV) by simple dissolution of the 1,2-oxazine N-oxide derivative in methanol or ethanol, since the undesirable Nef reaction which yields the corresponding diketo compound will otherwise take place as a competing reaction [cf. for example Tetrahedron 45, 2099 (1989)].

Some of the enamines of the formula (XXVI) are known, or they can be prepared for example from appropriately substituted acetophenones and cyclic amines by standard procedures (for example Org. Syntheses Vol. 58, 56, John Wiley & Sons, New York). Some of the acetophenones required are commercially available or known, or they can be prepared by known methods of the chemistry of aromatics.

Some of the nitrostyrenes of the formula (XXVII) are known, or they can be prepared for example by formylation of the nitromethylbezenes of the formula (XIX) given above (cf. for example Houben-Weyl, Methoden der Organischen Chemie, Georg Thieme Verlag Stuttgart, Volume E16, 215).

The novel aminoketones of the formula (II) can also be prepared for example by hydrolyzing imines of the formula (XXVIII) in a process (A c) according to the following scheme:

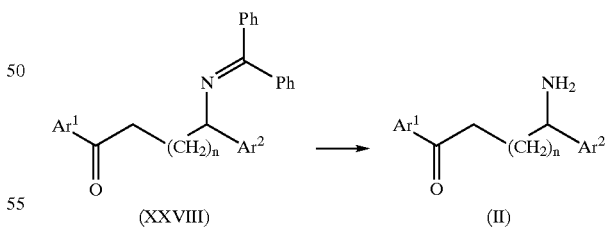

The hydrolysis can be carried out by generally known methods for example using aqueous hydrochloric acid. Here, the aminoketones of the formula (II) are also preferably isolated as their salts, for example as hydrochlorides, as described further above.

The imines of the formula (XXVIII) in which n equals 1 (XXVIII-a) can be prepared for example by carrying out Michael additions of N-diphenylmethylene-benzylamines of the formula (XXIX) to phenyl vinyl ketones of the formula (XX) according to the following scheme:

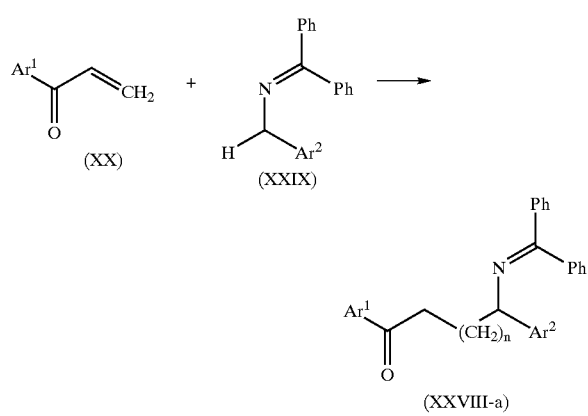

(XX)    (XXIX)

(XXVIII-a)

The addition is carried out in the presence of an acid binder and in the presence of a diluent such as, for example, acetonitrile or dichloromethane and, if appropriate, in the presence of a reaction auxiliary, for example at room temperature. A preferred acid binder is aqueous alkali such as 50% strength aqueous sodium hydroxide solution in the presence of a phase transfer catalyst such as, for example, triethylbenzylammonium chloride as reaction auxiliary [cf. for example Synth. Commun. 17, 211 (1987)], The preparation of the phenyl vinyl ketones of the formula (XX) is described further above. The N-dimethylmethylenebenzylamines of the formula (XXIX) are obtained for example by reacting the corresponding benzylamines with benzophenone (cf. for example Tetrahedron Lett. 1978, 2641). The benzylamines required for this purpose are known, or they can be prepared by known methods such as, for example, aminolysis of the corresponding benzyl halides (see above).

The cyclic O-methanesulphonyl oximes required for carrying out process (B) according to the invention are defined in a general way by the formula (III) In this formula $Ar^2$ and n both preferably have those meanings already mentioned in connection with the description of cyclic amines of the formula (I) as preferred The O-methanesulphonyl oximes of the formula (III) are novel.

The O-methylsulphonyl oximes of the formula (III) can be prepared for example by first converting cyclic a-aryl ketones of the formula (XXXI) by generally known methods into their oximes of the formula (XXX) and then reacting these with methanesulphonyl chloride by the method of the mesylation of alcohols according to the following scheme.

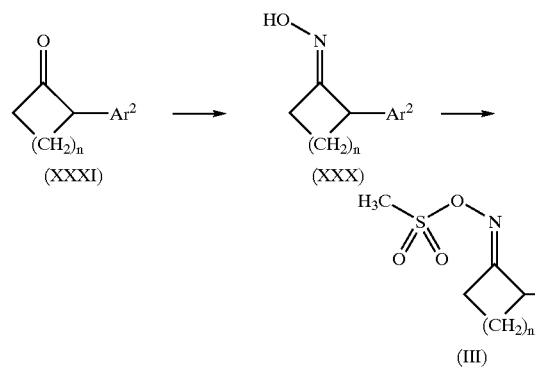

Cyclic α-aryl ketones of the formula (XXXI) can be prepared for example by epoxidizing 1-arylcycloalkenes of the formula (XXXIII) by conventional methods, for example using m-chloroperbenzoic acid, to give oxiranes of the formula (XXXII), and then isomerizing these by acid work-up according to the following scheme [cf. for example Tetrahedron 30, 2027 (1974)]:

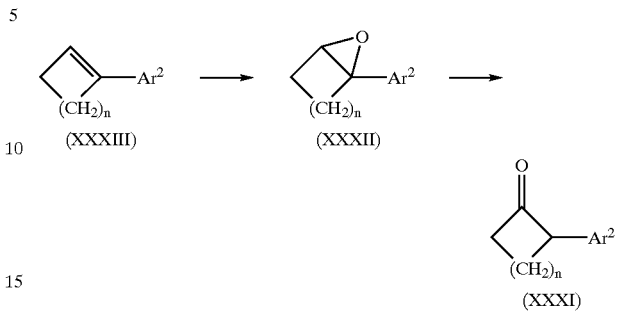

Of course it is also possible to isomerize oxiranes of the formula (XXXII) obtained by different routes to cyclic x-aryl ketones of the formula (XXXI), for example by shaking a solution in chloroform with 20% strength sulphuric acid.

1-arylcycloalkenes of the formula (XXXIII) can be prepared for example by reacting the aryl Grignard compounds of the formula (XIV) described further above with ketones of the formula (XXXV) under usual Grignard conditions and dehydrating the cyclic benzyl alcohols of the formula (XXXIV), for example obtained in this manner, according to the following scheme:

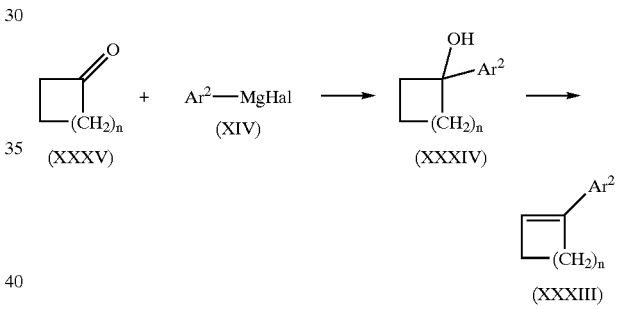

The dehydration can be carried out for example by dissolving the alcohol in a little of a polar solvent such as hexane and stirring with half-concentrated sulphuric acid, for example at 0° to 20° C. [cf. for example Tetrahedron 30, 2027 (1974)].

The ketones of the formula (XXXV), cyclobutanone, cyclopentanone and cyclohexanone are all commercially available.

The aryl Grignard compounds further required for carrying out process (B) according to the invention are defined in a general way by the formula (IV) In this formula, $Ar^1$ preferably has that meaning already mentioned in connection with the description of the cyclic imines of the formula (I) as preferred.

Aryl Grignard compounds of the formula (IV) are known, or they can be prepared by Grignard reaction from the corresponding aryl halides and magnesium. Aryl halides are generally known compounds of organic chemistry.

The cyclic imines of the formula (V) required for carrying out process (C) according to the invention are, in as far as $X^1$ represents bromine or iodine, subsets of the compounds of the general formula (I) according to the invention and can be prepared for example by process (A) or (B). If $X^1$ represents trifluoromethanesulphonyl, the compounds of the formula (V-a) can be prepared by reaction of hydroxyl compounds of the formula (I-f) which can also be prepared by process (A) or (B) using trifluoromethanesulphonyl chloride or trifluoromethanesulphonic anhydride in the presence of an acid binder such as, for example, pyridine and if appropriate in the presence of a diluent according to the following scheme:

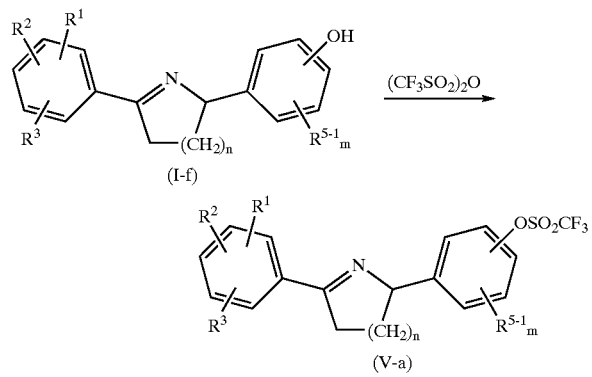

The boronic acids also required for carrying out process (C) according to the invention are defined in a general way by the formula (VI). In this formula, $R^{4-1}$ preferably has that meaning already mentioned in connection with the description of the cyclic imines of the formula (I-b) as preferred.

Aromatic boronic acids of the formula (VI) are known, or they can be prepared by known methods [cf. Chem. Rev. 45, 2457 (1995); Pure Appl. Chem. 66, 213 (1994)].

The cyclic imines of the formula (I-d) required for carrying out process (D) according to the invention are subsets of the compounds of the general formula (I) according to the invention and can be prepared for example by processes (A) to (C).

The compounds further required for carrying out process (D) according to the invention are defined by formula (VII). In this formula, $R^{15}$, $R^{16}$, G, p, q and r each preferably have those meanings already mentioned in connection with the description of the cyclic imines of the formula (I) as preferred Ab represents a conventional leaving group such as, for example, halogen, in particular chlorine or bromine; alkylsulphonyloxy, in particular methylsulphonyloxy, or optionally substituted arenesulphonyloxy, in particular phenylsulphonyloxy, p-chlorosulphonyloxy or p-tolylsulphonyloxy.

The compounds of the formula (VII) are generally known compounds of organic chemistry.

If appropriate, the process (A) according to the invention is carried out in the presence of a suitable acid acceptor. Suitable acid acceptors are all conventional inorganic or organic bases. These include preferably alkaline earth metal or alkali metal hydroxides, amides, alkoxides, acetates, carbonates or bicarbonates, such as, for example, sodium hydroxide, potassium hydroxide or ammonium hydroxide, sodium amide, lithium diisopropylamide, sodium methoxide, sodium ethoxide, potassium tert-butoxide, sodium acetate, potassium acetate, calcium acetate or ammonium acetate, sodium carbonate, potassium carbonate or ammonium carbonate, sodium bicarbonate or potassium bicarbonate, and tertiary amines, such as trimethylamine, triethylamine, tributylamine, N,N-dimethylaniline, N,N-dimethylbenzylamine, pyridine, N-methyl-piperidine, N-methylmorpholine, N,N-dimethylaminopyridine, diazabicyclooctane (DABCO), diazabicyclononene (DBN) or diazabicycloundecene (DBU)

If appropriate, the process (A) according to the invention is carried out in the presence of a diluent. Suitable diluents are water, organic solvents and mixtures thereof. Examples include: aliphatic, alicyclic or aromatic hydrocarbons, such as, for example petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloroethane, trichloroethane or tetrachloroethylene; ethers, such as diethyl ether, diisopropyl ether, methyl t-butyl ether, methyl t-amyl ether, dioxan, tetrahydrofuran, 1,2-dimethoxyethane, 1,2-diethoxyethane, diethylene glycol dimethyl ether or anisole; ketones, such as acetone, butanone, methyl isobutyl ketone or cyclohexanone; nitriles, such as acetonitrile, propionitrile, n- or 1-butyronitrile or benzonitrile; amides, such as formamide, N,N-dimethylformamide, N,N-dimethylacetamide, N-methylformanilide, N-methylpyrrolidone or hexamethylphosphoric triamide; N-oxides such as N-methylmorpholine N-oxide, esters such as methyl acetate, ethyl acetate or butyl acetate; sulphoxides, such as dimethyl sulphoxide; sulphones, such as sulpholane; alcohols, such as methanol, ethanol, n- or i-propanol, n-, iso-, sec- or tert-butanol, ethanediol, propane-1,2-diol, ethoxyethanol, methoxyethanol, diethylene glycol monomethyl ether, diethylene glycol monoethyl ether, water.

The reaction temperature of the process (A) according to the invention can be varied within a relatively wide range. Generally, the process is carried out at temperatures between –50° C. and +150° C., preferably between –20° C. and +100° C.

In the process (A) practice according to the invention, the salt of the compound of the formula (II) and the base are generally employed in equimolar amounts.

In a preferred variant of the process, the aminoketone of the formula (II) is prepared by one of the routes (A.a) to (A.c) and cyclocondensed without isolation in a one-pot reaction by addition of a base according to process (A).

Suitable diluents for carrying out process (B) according to the invention are inert organic solvents and mixtures thereof. Examples include: aliphatic, alicyclic or aromatic hydrocarbons such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloroethane, trichloroethane or tetrachloroethylene; ethers, such as diethyl ether, diisopropyl ether, methyl t-butyl ether, methyl t-amyl ether, dioxane, tetrahydrofuran, 1,2-dimethoxyethane, 1,2-diethoxyethane, diethylene glycol dimethyl ether or anisole.

Preference is given to employing a solution of the Grignard compound of the formula (IV) in an ether and a solution of the O-methylsulphonyl oxime of the formula (III) in a hydrocarbon.

The reaction temperature of the process (B) according to the invention can be varied within a relatively wide range. Generally, the reaction is carried out at temperatures between –100° C. and +50° C., preferably between –80° C. and +30° C.

In the practice of process (B) according to the invention, the Grignard compound of the formula (IV) and the O-methylsulphonyl oxime of the formula (III) are employed in a molar ratio of 1:1 to 3:1, preferably 1:1 to 2:1.

Suitable catalysts for carrying out process (C) according to the invention are palladium (0) complexes. Preference is given for example to tetrakis(triphenylphosphine)palladium.

Suitable acid acceptors for carrying out process (C) according to the invention are inorganic or organic bases. These include preferably alkaline earth metal or alkali metal hydroxides, acetates, carbonates or bicarbonates, such as, for example, sodium hydroxide, potassium hydroxide, barium hydroxide or ammonium hydroxide, sodium acetate, potassium acetate, calcium acetate or ammonium acetate, sodium carbonate, potassium carbonate or ammonium carbonate, sodium bicarbonate or potassium bicarbonate, alkali metal fluorides, such as, for example, caesium fluoride, and tertiary amines, such as trimethylamine, triethylamine, tributyl amine, N,N-dimethylaniline, N,N-dimethylbenzylami ne, pyridi ne, N-methylpiperidine, N-methylmorpholine, N,N-dimethylaminopyridine, diazabicyclooctane (DABCO), diazabicyclononene (DBN) or diazabicycloundecene (DBU)

Suitable diluents for carrying out process (C) according to the invention are water, organic solvents and mixtures thereof. Examples include: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloroethane, trichloroethane or tetrachloroethylene; ethers, such as diethyl ether, diisopropyl ether, methyl t-butyl ether, methyl t-amyl ether, dioxan, tetrahydrofuran, 1,2-dimethoxyethane, 1,2-diethoxyethane, diethylene glycol dimethyl ether or anisole; alcohols, such as methanol, ethanol, n- or i-propanol, n-, iso-, sec- or tert-butanol, ethanediol, propane-1,2-diol, ethoxyethanol, methoxyethanol, diethylene glycol monomethyl ether, diethylene glycol monoethyl ether.

The reaction temperature of process (C) according to the invention can be varied within relatively wide ranges. Generally, the process is carried out at temperatures between 0° C. and +140° C., preferably between 50° C. and +100° C.

In the practice of process (C) according to the invention, the boronic acid of the formula (VI) and the compound of the formula (V) are employed in a molar ratio of 1:1 to 3:1, preferably 1:1 to 2:1. Generally, 0005 to 0.5 imiol, preferably 0.01 mol to 0.1 mol of catalyst are employed per mole of the compound of the formula (V). An excess of base is generally employed The process (D) according to the invention is preferably carried out in the presence of a suitable acid acceptor. Suitable acid acceptors are all conventional inorganic or organic bases. These include preferably alkaline earth metal or alkali metal hydrides, hydroxides, amides, alkoxides, acetates, carbonates or bicarbonates, such as, for example, sodium hydride, sodium hydroxide, potassium hydroxide or ammonium hydroxide, sodium amide, lithium diisopropylamide, sodium methoxide, sodium ethoxide, potassium tert-butoxide, sodium acetate, potassium acetate, calcium acetate or ammonium acetate, sodium carbonate, potassium carbonate or ammonium carbonate, sodium bicarbonate or potassium bicarbonate, and tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

The process (D) according to the invention can be carried out in the presence of a suitable phase transfer catalyst. Examples of these catalysts include: tetrabutylammonium iodide, tetrabutylammonium bromide or tetrabutylammonium chloride, tributylmethylphosphonium bromide, trimethyl-$C_{13}$–$C_{15}$-alkylammonium chloride or trimethyl-$C_{13}$–$C_{15}$-alkylammonium bromide, dibenzyldimethylammonium methylsulphate, dimethyl-$C_{12}$–$C_{14}$-alkylbenzylammonium chloride, 15-crone-S, 18-crone-6 or tris-[2-(2-methoxyethoxy)-ethyl]-amine.

The process (D) according to the invention is preferably carried out in the presence of a diluent. Suitable diluents are for example all solvents listed under process (A).

The reaction temperature of process (D) according to the invention can be varied within a relatively wide range. Generally, the reaction is carried out at temperatures between −20° C. and +100° C., preferably between 0° C. and 60° C.

In the practice of process (D) according to the invention, approximately equimolar amounts of the starting materials are generally employed. However, it is also possible to employ an excess of the compound of the formula (VII)

The reactions of the process E) according to the invention are derivatization reactions in particular of carboxylic esters and ketones known to the person skilled in the art (cf. for example Houben-Weyl, Methoden der organischen Chemie, Georg Thieme Verlag, Stuttgart, Vol. VII/2, in particular 1912 ff; Vol. VIII for carboxylic esters and derivatives thereof; Vol. E5, in particular p. 812 ff and literature cited therein).

The reactions of the processes according to the invention can be carried out at atmospheric pressure or at elevated pressure, preference is given to working at atmospheric pressure. Work-up is carried out by customary methods of organic chemistry. The end products are preferably purified by crystallization, chromatographic purification or by removing the volatile components, if appropriate under reduced pressure.

The active compounds are suitable for controlling animal pests, in particular insects, arachnids and nematodes, encountered in agriculture, in forestry, in the protection of stored products and of materials, and in the hygiene field, and have good plant tolerance and low toxicity to warm-blooded animals. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera spec.*

From the order of the Symphyla, for example, *Scutigerella immaculata.*

From the order of the Thysanura, for example, *Lepisma saccharina.*

From the order of the Collembola, for example, *Onychiurus armatus*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schi stocerca gregaria.*

From the order of the Dermaptera, for example, *Forficula auricularia*

From the order of the Isoptera, for example, Reticulitermes spp

From the order of the Anoplura, for example, *Pediculus humanus corporis,* Ilaematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix*, Pemphigus spp., *Macrosiphum avenae*, Myzus spp, *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidielia aurantii, Aspidiotus hederae*, Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euprostis chrysorrhoea*, Lymantria spp., *Bucculatrix thurberiella, Phyllocnistis citrella*, Agrotis spp., Euxoa spp., Feltia spp., *Earias insulana*, Heliothis spp, *Laphygma exigua, Mamestra brassicae, Panolis flammea, Prodenia litura*, Spodoptera spp., Trichoplusia ni, *Carpocapsa pomonella*, Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae*, Diabrotica spp, *Psylliodes chrysocephala, Epilachna varivestis*, Atomaria spp., *Oryzaephilus surinamensis*, Anthonomus spp., Sitopbliius spp., *Otiorrhynchus sulcatus, Cosmopolites sordidus, Ceuthorrhynchus assimilis, Hypera postica*, Dermestes spp., Trogoderma spp., Anthrenus spp, Attagenus spp., Lyctus spp, *Meligetlies aeneus*, Ptinus spp., *Niptus hololeucus, Gibbium psylloides*, Tribolium spp, *Tenebrio molitor*, Agriotes spp., Conoderus spp., *Melolontha melolontha, Amphimallon soistitialis* and *Costelytra zealandica*.

From the order of the Hymenoptera, for example, Diprion spp., Hoplocampa spp, Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp.

From the order of the Arachnida, for example, *Scorpio maurus, Latrodectus mactans*.

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp., Tetranychus spp.

The phytoparasitic nematodes include Pratylenchus spp., *Radopholus similis, Ditylenchus dipsaci, Tylenchulus semipenetrans*, Heterodera spp., Meloidogyne spp., Aplelenchoides spp., Longidorus spp., Xiphinema spp., Trichodorus spp.

The active compounds of the formula (I) according to the invention in particular have outstanding activity against mustard beetle larvae (*Phaedon cochleariae*), caterpillars of the owlet moth (*Spodoptera frugiperda*), larvae of the green rice leaf hopper (*Neplhotettix cincticeps*), green peach aphids (*Myzus persicae*) and all stages of the common spider mite (*Tetranychus urticae*).

The active compounds can be converted to the customary formulations, such as solutions, emulsions, wettable powders, suspensions, powders, dustin(g agents, pastes, soluble powders, granules, suspension emulsion concentrates, natural and synthetic materials impregnated with active compound and very fine capsules in polymeric substances.

These formulations are produced in a known manner, for example preferably by mixing the active compounds with extenders, that is liquid solvents and/or solid carriers, if appropriate with the use of surface-active agents, that is emulsifying agents and/or dispersing agents and/or foam-forming agents.

In the case of the use of water as an extender, organic solvents can, for example, also be used as auxiliary solvents. Suitable liquid solvents are essentially. aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

Suitable solid carriers are:

for example ammonium salts and ground natural minerals, such as kaolins, clays, talc, chalk, quartz, attapulgite, montmorillonite or diatomaceous earth, and ground synthetic minerals, such as highly disperse silica, alumina and silicates; suitable solid carriers for granules are: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; suitable emulsifying and/or foam-forming agents are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysis products, suitable dispersing agents are: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as ceplhalins and lecithins, and synthetic phospholipids, can be used in the formulations Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

Examples of particularly advantageous mixing components are the following:

Fungicides:
2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate, methyl (E)-methoximino[alpha-(o-tolyloxy)-o-tolyl]acetate, 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezine, dicloran, diethofencarb, difenoconazole, dimethirimol, dimethomorplh, diniconazole, dinocap, diphenylamine, dipyrithione, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tectoftalam, tecnazene, tetraconazole, thitabendazole, thicyofen, thiophanate-methyl, thiram, tolclofos-methyl, tolylfluanid, triadimefon, triadimenol, triazoxide, trichiamide, tricyclazole, tridemorph, triflumizole, triforine, triticonazole, validamycin A, vinclozolin, zineb, ziram.

Baictericides:

bronopol, dichliorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations Insecticides/Acaricides/Nematicides:

abamectin, AC 303 630, acephate, acrinathrin, alanycarb, aldicarb, alphamethrin, amitraz, avermectin, AZ 60541, azadirachtin, azinphlos A, azinphos M, azocyclotin, Bacillus thuringiensis, bendiocarb, benfuracarb, bensultap, beta-cyfluthrin, bifenthrin, BPMC, brofenprox, bromophos A, bufencarb, buprofezin, butocarboxim, butylpyridaben, cadusafos, carbaryl, carbofuran, carbophenothion, carbosulfan, cartap, CGA 157419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimfos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonofos, formothion, fosthiazate, fubfenprox, furathiocarb, HCH, heptenophos, hexaflumuron, hexythiazox, imidacloprid, iprobenfos, isazofos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, $NC_{184}$, NI 25, nitenpyram, omethoate, oxamyl, oxydemeton M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozine, pyrachllofos, pyridaphenthion, pyresmnethrin, pyrethrum, pyridaben, pyrimidifen, pyriproxyfen, quinalphos,

RH 5992, salithion, sebufos, silafluofen, sulfotep, suiprofos, tebufenozide, tebufenpyrad, tebupirimifos, teflubenzuron, tefluthrin, temeplhos, terbam, terbufos, tetrachlorvinplhos, thiafenox, tIliodicarb, thiofanox, tiliomietlhon, thionazin, thuringiensin, tralomethrin, triarathene, triazophos, triazuron, triclhlorfon, triflumuron, trimethacarb, vamidothion, XMC, xylylcarb, YI 5301/5302, zetamethrin.

A mixture with other known active ingredients, such as herbicides, or with fertilizers and growth-regulators is also possible.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound has an excellent residual action on wood and clay as well as a good stability to alkali on limed substrates.

The active compounds according to the invention are not only active against plant, hygiene and stored-product pests, but also, in the veterinary medicine sector, against animal parasites (ectoparasites), such as ixodid ticks, argasid ticks, scab mites, trombiculid mites, flies (stinging and sucking), parasitic fly larvae, lice, hair lice, bird lice and fleas. These parasites include:

From the order of the Anoplurida, for example, Haematopinus spp., Lino(nathus spp., Pediculus spp., Phtirus spp. and Solenopotes spp From the order of the Mallophagida and the sub-orders Amblycerina and Ischnocerina, for example, Trimenopon spp, Menopon spp, Trinoton spp, Bovicola spp., Werneckietla spp., Lepikentron spp, Damalina spp., Trichodectes spp. and Felicola spp.

From the order of the Diptera and the sub-orders Nematocerina and Brachycerina, for example, Aedes spp., Anopheles spp., Culex spp., Simulium spp, Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp, Lucilia spp., Chrysomyia spp., Wohlfahrtia spp., Sarcophaga spp., Oestrus spp., Hypoderma spp., Gasterophilus spp, Hippobosca spp., Lipoptena spp. and Melophagus spp.

From the order of the Siphonapterida, for example, Pulex spp, Ctenocephalides spp., Xenopyslla spp. and Ceratophyllus spp.

From the order of the Heteropterida, for example, Cimex spp, Triatoma spp., Rhodnius spp. and Panstrongylus spp.

From the order of the Blattarida, for example, *Blatta orientalis, Periplaneta americana, Blattela germanica* and Supella spp.

From the sub-class of the Acaria (Acarida) and the orders of the Meta- and Mesostigmata, for example, Argas spp., Ornithodorus spp., Otabius spp, Ixodes spp., Amblyomma spp., Boophilus spp., Dermacentor spp, Haemaphysalis spp, Hyalomma spp., Rhipicephalus spp, Dermanyssus spp., Raillietia spp., Pneumonyssus spp., Sternostoma spp. and Varroa spp.

From the order of the Actinedida (Prostigmata) and Acaridida (Astigmata), for example, Acarapis spp, Cheyletiella spp, Ornithocheyletia spp., Myobia spp., Psorergates spp., Demodex spp., Trombicula spp, Listrophorus spp., Acarus spp., Tyrophagus spp, Caloglyphus spp., Hypodectes spp., Pteroliclius spp., Psoroptes spp., Chorioptes spp., Otodectes spp, Sarcoptes spp., Notoedres spp Knemidocoptes spp., Cytodites spp. and Laminosioptes spp.

For example, they have an outstanding activity against all larval stages of the fly *Lucilia cuprina* and all development stages of the tick *Amblyomma variegatum.*

The active compounds of the formula (I) according to the invention are also suitable for controlling arthropods which attack agricultural livestock, such as, for -example, cattle, sheep, goats, horses, pigs, donkeys, camels, buffalo, rabbits, chickens, turkeys, ducks, geese, honey bees, other domestic animals, such as, for example, dogs, cats, caged birds, aquarium fish, and so-called experimental animals, such as, for example, hamsters, guinea-pigs, rats and mice. By controlling these arthropods, it is intended to reduce deaths and decreased performances (in meat, milk, wool, hides, eggs, honey and the like), so that more economical and simpler animal keeping is made possible by using the active compounds according to the invention.

In the veterinary sector, the active compounds according to the invention are used in a known manner by enteral administration, for example in the form of tablets, capsules, drinks, drenches, granules, pastes, boluses, the feed-through method, suppositories, by parenteral administration, such as, for example, by means of injections (intramuscular, subcutaneous, intravenous, intraperitoneal and the like), implants, by nasal administration, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds of the formula (I) can be used as formulations (for example powders, emulsions, flowables) which comprise the active compounds in an amount of 1 to 80% by weight, either directly or after dilution by a factor of 100 to 10 000, or they may be used in the form of a chemical bath.

Furthermore, it has been found that the compounds of the formula (I) according to the invention have a potent insecticidal action against insects which destroy industrial materials.

The following insects may be mentioned by way of preferred examples bLit without any limitation:

Beetles, such as

*Hylotrupes bajulus, Chlorophlorus pilosis, Anobium punctatum, Xestobitin rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis,* Xyleborus spec., Tryptodendron spec., *Apate monachus, Bostrychus capucins, Heterobostrychus brunneus,* Sinoxylon spec. and *Dinoderus minutus.*

Dermapterans, such as

*Sirex juvencus, Urocerus gigas, Urocerus gigas taignus* and *Urocerus augur.*

Termites, such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus.*

Bristletails, such as *Lepisma saccharina.*

Industrial materials are to be understood as meaning, in the present context, non-live materials, such as, preferably, synthetic materials, glues, sizes, paper and board, leather, wood and timber products, and paint.

The materials to be very particularly preferably protected against attack by insects are wood and timber products.

Wood and timber products which can be protected by the composition according to the invention or mixtures comprising such a composition are to be understood as meaning, for example, construction timber, wooden beams, railway sleepers, bridge components, jetties, wooden vehicles, boxes, pallets, containers, telephone poles, wood lagging, windows and doors made of wood, plywood, particle board, joiner's articles, or wood products which, quite generally, are used in the construction of houses or in joinery, The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colorants and pigments and other processing auxiliaries.

The insecticidal compositions or concentrates used for the protection of wood and wooden materials comprise the active compound according to the invention at a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-like solvents having an evaporation number of above 35 and a flashpoint of above 30° C., preferably above 45° C. Substances which are used as such oily and oil-like solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of turpentine and the like.

In a preferred embodiment, liquid aliphatic hydrocarbons with a boiling ran Me of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-like solvents of low volatility and having an evaporation number of above 35 and a flashpoint of above 30° C., preferably above 45° C., can be partially replaced by organochemical solvents of high or medium volatility, with the proviso that the solvent mixture also has an evaporation number of above 35 and a flashpoint of above 30° C., preferably above 45° C., and that the insecticide/fungicide mixture is soluble or emulsifiable in this solvent mixture.

In a preferred embodiment, part of the organochemical solvent or solvent mixture is replaced by an aliphatic polar organochemical solvent or solvent mixture Substances which are preferably used are aliphatic organochemical solvents having hydroxyl and/or ester and/or ether groups, such as, for example, glycol ether, esters and the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/coumarone resin, silicone resin, drying vegetable and/or drying, oils and/or physically drying binders based on a natural and/or synthetic resin.

The artificial resin used as the binder can be employed in the form of an emulsion, dispersion or solution. Up to 10% by weight of bitumen or bituminous substances can also be used as binder. In addition, colorants, pigments, water repellents, odour-masking substances and inhibitors or anti-corrosives known per se and the like can also be employed.

The composition or the concentrate preferably comprises, in accordance with the invention, at least one alkyd resin or modified alkyd resin and/or a drying vegetable oil as the organochemical binder Preferably used according to the invention are alkyd resins with an oil content of over 45% by weight, preferably 50 to 68% by weight All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed).

The plasticizers are from the chemical classes of the phthalic esters, such as dibutyl phthalate, dioctyl phthalate or benzylbutyl phthalate, the phosphoric esters, such as tributyl phosphate, the adipic esters, such as di-(2-ethylhexyl) adipate, the stearates, such as butyl stearate or amyl stearate, the oleates, such as butyl oleate, the glycerol ethers or relatively high-molecular-weight glycol ethers, glycerol esters and p-toluenesulphonic esters.

Fixatives are chemically based on polyvinyl alkyl ethers, such as, for example, polyvinyl methyl ether, or ketones, such as benzophenone or ethylenebenzophenone.

Particularly suitable as a solvent or diluent is also water, if appropriate as a mixture with one or more of the abovementioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise other insecticides and, if appropriate, additionally one or more fungicides.

Suitable additional components which may be admixed are, preferably, tlhe insecticides and fungicides mentioned in WO 94/29 268 The compounds mentioned in that document are expressly incorporated into the present application.

Very particularly preferred components which may be admixed are insecticides, such as chlorpyrifos, phoxim, silafluofin, alphamethrin, cyfluthl-in, cypermethirin, deltamethirin, permethrin, imidacloprid, NI-25, flufenoxuron, hexaflumuron and triflumuron, and fungicides, such as epoxyconazole, hexaconazole, azaconazole, propiconazole, tebuconazole, cyproconazole, metconazole, imazalil, dichlorfluanid, -tolylfluanid, 3-iodo-2-propinyl-butyl carbamate, N-octyl-isothiazolin-3-one and 4,5-dichloro-N-octylisothiazolin-3-one.

The preparation and the use of the active compounds according to the invention can be seen from the examples which follow.

PREPARATION EXAMPLES

Example I-1

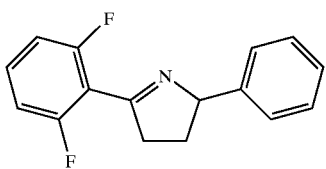

At 0° C., 0.825 g of 1-′butoxycarbonylamino-3-(2,6-difluorobenzoyl)-1-phenylpropane (for example by the method of Ex. VIII–I) were admixed dropwise with 1.6 ml of trifluoroacetic acid. The mixture was allowed to warm to room temperature and stirred for a further 3 h. At 0° C., the mixture was then made alkaline (pH 11) using 1N of aqueous sodium hydroxide solution. The mixture was extracted three times with ethyl acetate and the combined extracts were dried over sodium sulphate and evaporated under reduced pressure. 0.45 g (83% of theory) of 2-(2,6-difluorophenyl)-5-phenyl-3,4-dihydro-2H-pyrrole was obtained.

$^1$H NMR (400 MHz, CDCl$_3$) δ [ppm]: 1.75 (m, 1H, CHHCHPh); 2.85 (m, 1H, CHHCHPh); 3.00 (m, 2H, CH$_2$CN); 5.80 (t, 1H, NCHPh); 7.20–7.40 (m, 7H, ArH); 7.57 (m, 1H, ArH) (Ph=phenyl).

Example I-2

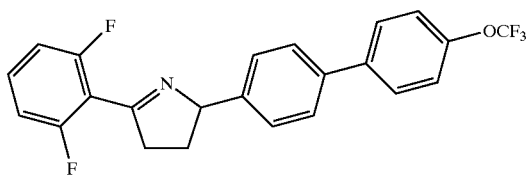

By the method of I-1, 0.36 g (96% of theory) of 2-(2,6-diflorophlenyl)-5-(4'-trifluoromethoxybiphenyl-4-yl)-3,4-dihydro-2H-pyrrole was obtained from 0.38 g of 1-′butoxycarbonylamino-3-(2,6-difluorobenzoyl)-1-(4'-trifluoromethoxybi phenyl-4-yl)-propane (for example by the method of Ex. VTII-2)

$^1$H NMR (500 MHz, CDCl$_3$) δ [ppm] 2.10 (m, 1H); 2.75 (m, 111), 3.29 (t, 2H), 5.59 (t, 1H); 7.05 (t, 2H); 7.29 (d. J~8 Hz, 2H); 7.42 (d J=7.4 Hz, 211), 7.47 (m 1H); 7.58 (d. J=7.4 Hz, 2H), 7.60 (d. J=7.4 Hz, 2H)

Example I-3

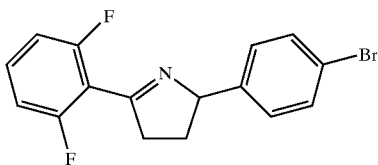

By the method of I-1, 2.24 g (41% of theory) of 2-(2,6-difluorophenyl)-5-(4-bromophenyl)-3,4-dihydro-2H-pyrrole were obtained from 7.45 g of 1-′butoxycarbonylamino-3-(2,6-difluorobenzoyl)-1-(4-bromophenyl)-propane (for example by the method of Ex. VIII-3).

$^1$H NMR (400 MHz, CDCl$_3$) δ [ppm]. 1.70 (m, 1H, CHHCHPh); 2.58 (m, 1H, CHHCHPh); 3.00 (m, 2H, CH$_2$CN); 5.29 (t, 1H, NCHPh); 7.2–7.3 (m, 5H, ArH); 7.56 (m, 4H, ArH).

Example I-4

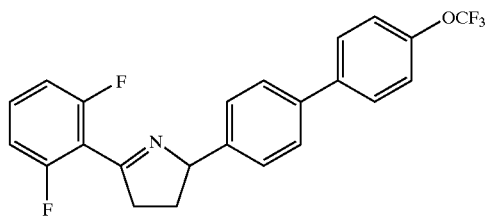

2.02 g of 2-(2,6-difluorophenyl)-5-(4-bromophenyl)-3,4-dihydro-2H-pyrrole (for example from Ex. I-3) were charged initially in 20 ml of dimethoxyethane under argon. 2.02 g of 4-trifluoromethoxyboronic acid and 0.346 g of tetrakis(triphenylphosphine)palladium were added successively, After 15 min, 9.6 ml of 2M aqueous sodium carbonate solution were added and the mixture was heated to 80° C. and stirred overnight. After the reaction had ended, the mixture was taken up in water/ethyl acetate, the phases were separated and the aqueous phase was extracted twice with about 100 ml of ethyl acetate each time. The combined organic phases were washed with saturated aqueous sodium chloride solution and dried over magnesium sulphate. Evaporation gave 1.90 g (76% of theory) of 2-(2,6-dlfluoroplienyl)-5-(4'-trifluorometloxybiphenyt-4-yi)-3,4-dlhydro-2H-pyrrole (cf. Ex. I-2)

The following compounds of the formula (I-f) are obtained analogously to Ex. No. I-4 and in accordance with the general preparation instructions.

TABLE 1

| Ex. No. | R$^4$ | ret.-time* [min] | ESI-MS**: m/z; [M + H]$^+$ |
|---|---|---|---|
| I-5 | (CH$_2$)$_3$CH$_3$ | 13.28 | 314.1 |
| I-6 | —C$_6$H$_4$—CH(CH$_3$)$_2$ | 14.73 | 376.0 |
| I-7 | —C$_6$H$_3$(Cl)$_2$ (3,5-diCl) | 16.68 | 401.9 |
| I-8 | —C$_6$H$_4$—F | 14.5 | 352.0 |

TABLE 1-continued
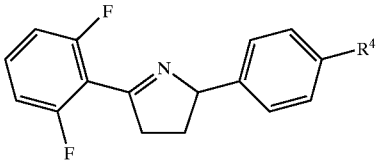
| Ex. No. | R⁴ | ret.-time* [min] | ESI-MS**: m/z; [M + H]⁺ |
|---|---|---|---|
| I-9 | 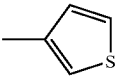 | 15.48 | 368.0 |
| I-10 | 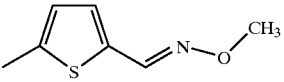 | 14.27 | 340.0 |
| I-11 | 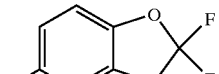 | 14.52 | 397.0 |
| I-12 | 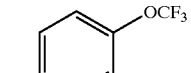 | 15.99 | 414.0 |
| I-13 | 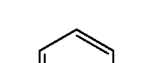 | 15.36 | 435.9 |
| I-14 | 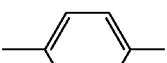 | 15.28 | 401.9 |
| I-15 | 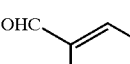 | 16.36 | 401.9 |
| I-16 | 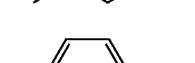 | 13.54 | 362.0 |
| I-17 | 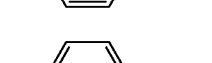 | 13.68 | 362.0 |
| I-18 | 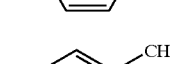 | 13.34 | 378.0 |
| I-19 | 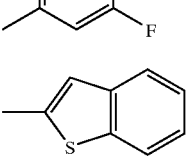 | 13.53 | 366.0 |
| I-20 | 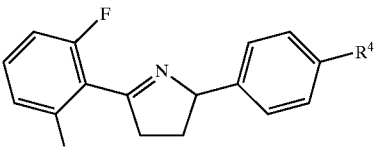 | 16.08 | 390.0 |
TABLE 1-continued
| Ex. No. | R⁴ | ret.-time* [min] | ESI-MS**: m/z; [M + H]⁺ |
|---|---|---|---|
| I-21 | 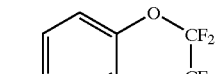 | 14.63 | 463.9 |
| I-22 | 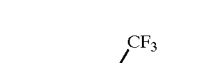 | 15.2 | 469.9 |
| I-23 | 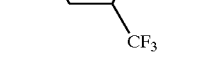 | 13.51 | 376.0 |
| I-24 | 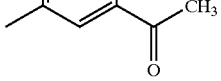 | 14.89 | 391.0 |
| I-25 | 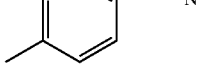 | 14.19 | 390.0 |
| I-26 | 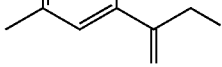 | 14.3 | 390.0 |
| I-27 | 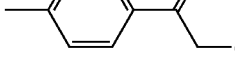 | 13.86 | 405.0 |
| I-28 | 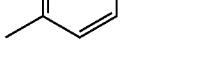 | 16 | 408.0 |
| I-29 |  | 13.52 | 392.0 |

TABLE 1-continued

![structure with difluorophenyl-pyrroline-phenyl-R4]

| Ex. No. | R⁴ | ret.-time* [min] | ESI-MS**: m/z; [M + H]⁺ |
|---|---|---|---|
| I-30 | (1-naphthyl-methyl) | 15.7 | 384.0 |
| I-31 | (aryl with C(CH₃)=N-O-CH₂CH₃) | 14.48 | 419.0 |
| I-32 | (aryl with C(CH₃)=N-O-CH₃ branched) | 16.24 | 419.0 |
| I-33 | (aryl-CH₂-CH(CH₃)₂) | 15.73 | 390.1 |
| I-34 | (aryl-CH₂-S-CH(CH₃)₂) | 16.22 | 422.0 |
| I-35 | (biphenyl) | 16.98 | 410.0 |
| I-36 | (aryl-(CH₂)₄-CH₃) | 17.33 | 418.1 |
| I-37 | (aryl-CH₂-O-aryl-Cl) | 17.1 | 473.9 |
| I-38 | (aryl-O-CH₂-aryl-Cl) | 17.24 | 473.9 |
| I-39 | (aryl-CH₃) | 15.1 | 348.0 |

TABLE 1-continued

![structure with difluorophenyl-pyrroline-phenyl-R4]

| Ex. No. | R⁴ | ret.-time* [min] | ESI-MS**: m/z; [M + H]⁺ |
|---|---|---|---|
| I-40 | (aryl-OCH₃) | 11.73 | 364.0 |
| I-41 | (aryl-C(O)-CH₃) | 10.93 | 376.0 |

*column: RP18 on silica gel (Kromasil), 1 = 125 mm, Ø = 3 mm, solvent: acetonitrile/water; gradient: t = 0 min 10/90 (vol/vol) => 18 min 100/0; flux: 1.5 ml min⁻¹
**electrospray-quadrupole-mass spectrometry Preparation of the Starting Materials γ-Ethoxy-γ-butyrolactam At 0° C., 9.91 g of succinimide were charged initially in 415 ml of ethanol and a total of 5.53 g of sodium boranate was added a little at a time. At this temperature, every 15 minutes 2 to 3 drops of 2N ethanolic hydrogen chloride were added dropwise over 4½ hours. Subsequently, the mixture was acidified to pH 3 using more acid. After stirring for 1 hour at 0° C., the mixture was neutralized using 1% strength ethanolic potassium hydroxide solution and the mixture was stirred for a further 15 minutes and evaporated. The residue was taken up in water and extracted three times with dichloromethane. After drying over sodium sulphate and concentrating, 7.16 g (55% of theory) of γ-ethoxy-γ-butyrolactam were obtained.

Example XI-1

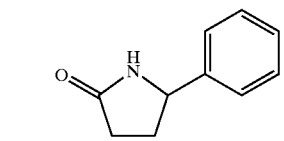

At 0° C., 6.45 g of γ-ethoxy-γ-butyrolactam and 50 ml of concentrated sulphuric acid were charged initially, and 18.8 ml of benzene were added. After thawing, the mixture was stirred at room temperature for 4 days. For work-up, the mixture was poured onto ice, extracted three times with ethyl acetate and the combined extracts were washed once with water and once with saturated aqueous sodium chloride solution, dried and evaporated. 8.1 g (100% of theory) of γ-phenyl-γ-butyrolactam were obtained.

¹H NMR (400 MHz, d₆ DMSO) δ [ppm]: 1.75 (m, 1H), 223 (t, 211); 245 (m, 1H); 4.67 (t, 1H); 7.26–7.39 (m, 5H), 8.08 (br, 1H).

Example XI-2

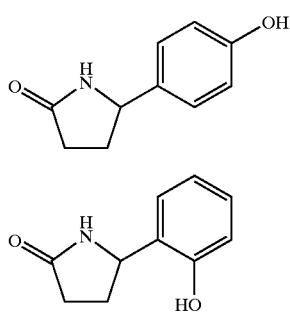

12.9 g of γ-ethoxy-γ-butyrolactam, 10 ml of concentrated sulphuric acid and 90 ml of glacial acetic acid were charged initially at 0° C. and admixed a little at a time with a total of 18.8 g of phenol. After thawing, the mixture was stirred at room temperature for 2 days. For work-up, the mixture was poured onto ice and extracted three times with ethyl acetate, and the combined extracts were washed once with water and once with saturated aqueous sodium chloride solution, dried and evaporated. After some time, γ-2-hydroxyphenyl-γ-butyrolactam (XI-2b) of melting point 220° C. (6.4 g, 36% of theory) crystallized from the aqueous phase. The residue obtained on evaporation was stirred with 1:1 mixture of cyclo-hexane/ethyl acetate and afforded on filtration with suction 4.65 g of γ-4-hydroxyphenyl-γ-butyrolactam (XI-2a) of melting point 183° C. The filtrate was evaporated. Recrystallization from dichloromethane/hexane gave a further 3.35 g (total 45% of theory) of γ-4-hydroxyphenyl-γ-butyrolactam.

Example XVII-2

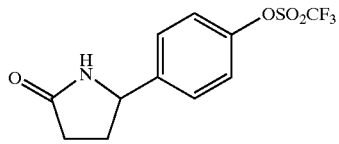

At 0° C., 10 g of trifluoromethanesulphonic anhydride were added dropwise to 5.23 g of γ-4-hydroxyphenyl-γ-butyrolactam (for example from Ex XI-2) in 60 ml of pyridine. After stirring overnight at room temperature, the reaction mixture was poured onto ice, acidified using 10% strength hydrochloric acid and extracted three times using ethyl acetate. After drying, and evaporation of the solvent, 6.4 g (70% of theory) of γ-4-trifluoromethylsulplionyloxyplienyl-γ-butyro-lactam of melting point 127° C. were obtained.

Example XI-a-2

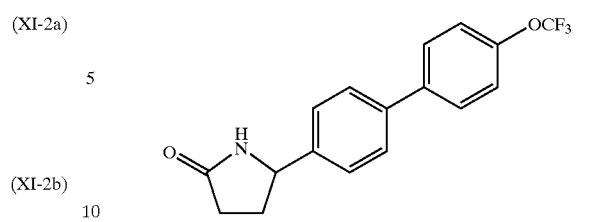

Under argon, 5.4 g of γ-4-trifluoromethylsulphonyloxyphenyl-γ-butyrolactam (for example from Ex. XVII-2) were charged initially in 43 ml of dimethoxyethane. In succession, 5.87 g of 4-trifluoromethoxyboronic acid and 1.01 g of tetrakis (triphenylphosphine)palladium were added. After 15 minutes, 28 ml of 2M aqueous sodium carbonate solution were added, the mixture was heated to 80° C. and stirred overnight. After the reaction had ended, the mixture was taken Up in water/ethyl acetate, the phases were separated and the aqueous phase was extracted twice with ethyl acetate. The combined organic phases were washed with saturated aqueous sodium chloride solution and dried. Evaporation gave 5.5 g (98% of theory) of γ-4'-trifluoromethoxybiphenyl-4-yl-γ-butyrolactam of melting point 128° C.

Example XI-3

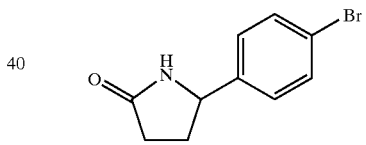

In a 3 l three-neck flask fitted with stirrer and distillation link, 199.3 g of ammonium formate in 127.9 g of formic acid were charged initially, and 210 g of 4-bromobenzoylpropionic acid which had been recrystallized from toluene were added. The flask was then immersed into a 200° C. oil bath At 60° C., the content of the flask began to dissolve with the evolution of gas. For about 2 hours, the mixture was subjected to distillation at a bottom temperature increasing from 140 to 167° C., until the reaction had ended. After cooling to below 60° C., 1 l of dichloromethane was added carefully and precipitated salt was separated off by filtration with suction through a nutsch filter The organic phase was washed with 1 l of water, dried over magnesium sulphate and concentrated under reduced pressure. For purification, the crude product was filtered through 1 kg of silica gel using dichloromethane/ethanol/triethylamine (95:5:3) and then crystallized from methyl tert-butyl ether. 38 g (19% of theory) of γ-4-bromophenyl-γ-butyrolactam of melting point 142° C. were obtained.

Example IX-1

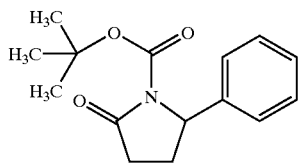

3.4 g of γ-phenyl-γ-butyrolactam (for example from Ex. XI-1) were charged initially in 63 ml of tetrahydrofuran (THF) and, at −78° C., admixed with 9.24 ml of a 2.4N butyllithium solution in n-hexane. The mixture was stirred at this temperature for half an hour, a solution of 5.04 g of di-tert-butyl dicarbonate in 20 ml of TiF was then added dropwise with continued cooling, and the mixture was stirred at −78° C. for a further 3 hours and then without cooling overnight The mixture was then hydrolysed using saturated aqueous ammonium chloride solution, diluted with water and extracted three times with ethyl acetate. The combined organic phases were washed with saturated aqueous sodium chloride solution and dried over magnesium sulphate. Evaporation gave 1.54 g (28% of theory) of N-$^t$butoxycarbonyl-γ-phenyl-γ-butyrolactam.

$^1$H NMR (400 MHz, $d_6$ DMSO) δ [ppm]: 1.18 (s, 9H); 1.73 (m, 1H); 240–2.60 (m, 3H); 5.10 (m, 1H); 7.24 (m, 2H); 7.30 (m, 1H); 7.38 (m, 2H)

Example IX-2

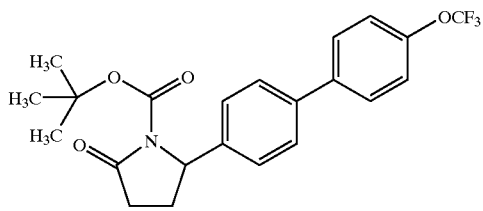

1.7 g of γ-4'-trifluoromethoxybiphenyl-4-yl-γ-butyrolactam (for example from Ex. XI-a-2) were charged initially in 30 ml of tetrahydrofuran (THE) and, at −78° C., admixed with 2.42 ml of a 2.4N butyllithium solution in n-hexane The mixture was stirred for half an hour at this temperature, and a solution of 1.27 g of di-tert-butyl dicarbonate in 10 ml of THF was then added dropwise witlh further cooling. The cooling was then removed and the mixture was stirred at room temperature overnight. The mixture was then hydrolysed using saturated aqueous ammonium chloride solution, acidified with 2N hydrochloric acid and extracted three times with dichloromethane. After drying and evaporation, the product was purified by column chromatography (stationary phase:silica gel; mobile phase:a gradient of cyclohexane:ethyl acetate =5:1.3 to 1.1:1). 1.14 g (47% of theory) of partly crystal line N-$^t$butoxycarbony-γ-4'-trifluoromethoxybiphenyl-4-yl-γ-butyrolactam were obtained.

$^1$H NMR (400 MHz, CDCl$_3$) δ [ppm]: 1.22 (s, 9H); 1.79 (m, 1H); 2.48–2.60 (m, 3H); 5.17 (m, 1H); 7.36 (d, 2H); 7.46 (d, 2H), 7.71 (d, 2H); 7.80 (d, 2H)

Example IX-3

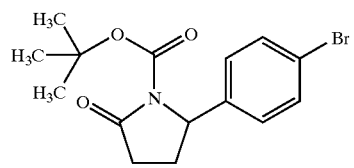

3.24 ml of diisopropylamine were charged initially in 90 ml of THF at −78° C. and admixed with 9.24 ml of a 2.4N butyllithium solution in n-hexane. The mixture was stirred for ½ hour at this temperature, and a solution of 5.02 g of γ-4-bromophenyl-γ-butyrolactam (for example from Example XI-3) in 20 ml of THF was then added dropwise. Stirring at −78° C. was continued for a further ½ h, and 5.04 g of di-tert-butyl dicarbonate in 20 ml of TtE were then added dropwise, the mixture was allowed to thaw and stirred at room temperature overnight. The mixture was then hydrolysed using saturated aqueous ammonium chloride solution, acidified with 2N hydrochloric acid and extracted three times with 150 ml of dichloromethane each time. After drying over magnesium sulphate and evaporation, the product was purified by crystallization from dichloromethane/hexane A total of 7.61 g (97% of theory) of crystalline N-$^t$butoxycarbonyl-γ-4-bromophenyl-γ-butyrolactam were obtained. The purest crystal fraction (2.34 g) melted at 122–124° C.

Example VIII-1

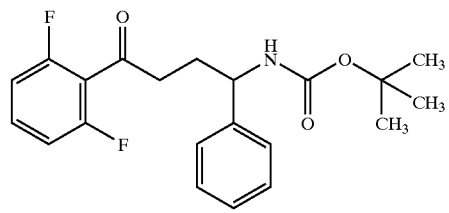

0.62 g of 1,3-difluorobenzene were charged initially in 15 ml of THF and, at −78° C., admixed with 2.4 ml of a 2.4N butyllithium solution in n-hexane. The mixture was stirred for 1 hour and, at this temperature, a solution of 1.44 g of N-$^t$butoxycarbonyl-γ-phenyl-γ-butyrolactam (for example from Ex. IX-1) in 7 ml of THF was then added very slowly dropwise. The mixture was stirred at −78° C. for 3 hours and then without cooling overnight. After hydrolysis using ammonium chloride solution, the mixture was extracted three times with ethyl acetate and the 10 combined extracts were dried and evaporated. Recrystallization from dichloromethane/hexane gave 1.03 g (50% of theory) of 1-$^t$butoxycarbonylamino-3-(2,6-di-fluorobenzoyl)-1-(4'-trifluoromethoxybiphenyl-4-yl)-propane.

$^1$H NMR (400 MHz, $d_6$ DMSO) δ [ppm]: 1.33 (s, 9H); 1.94 (m, 2H); 2.89 (t, 2H); 4.54 (m, 1H); 7.22 (m, 3H); 7.30 (m, 4H); 7.42 (br d, 1H); 7.60 (m, 1H)

Example VIII-2

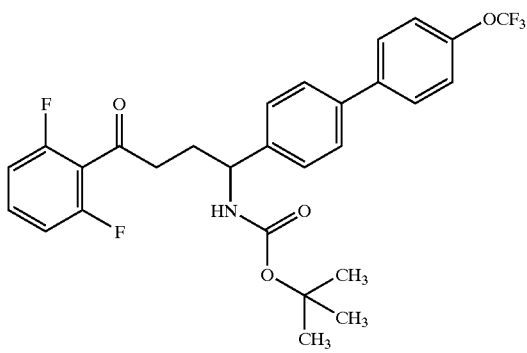

By the method of Example VIII-1, 2.23 g (77% of theory) of 1-*t*butoxycarbonylamino-3-(2,6-difluorobenzoyl)-1-(4'-trifluoromethoxybiphenyl-4-yl)-propane were obtained as an oil from 0.62 g of 1,3-difluorobenzene and 1.7 g of N-*t*butoxy-carbonyl-γ-4'-trifluoromethoxybiphenyl-4-yl-γ-butyrolactam (for example from Ex. IX-2).

$^1$H NMR (400 MHz, CDCl$_3$) δ [ppm]: 1.40 (s, 9H); 2.20 (m, 2H); 2.97 (m, 2H); 4.75 (m, 1H); 6.93 (t, 2H); 7.28 (m, 3H); 7.38 (d, 2H); 7.53 (d, 2H); 7.58 (d, 2H).

Example VIII-3

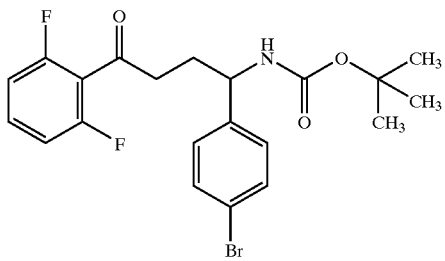

By the method of Example VIII-1, 2.51 g (93% of theory) of 1-*t*butoxycarbonyl-amino-3-(2,6-difluorobenzoyl)-1-(4-bromophenyl) propane with a melting range of 111–115° C. were obtained from 0.62 g of 2,3-difluorobenzene and 2,03 g of N-*t*butoxycarbonyl-γ-4-bromophenyi-γ-butyrolactam (for example from Ex. IX-3)

USE EXAMPLES

Example A
Phaedon Larvae Test

| Solvent: | 7 parts by weight of | dimethylformamide |
|---|---|---|
| Emulsifier: | 1 part by weight of | alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*), while the leaves are still moist.

After the desired period of time, the destruction in % is determined. 100% means that all the beetle larvae have been killed; 0% means that none of the beetle larvae have been killed.

In this test, for example the compound of Preparation Example I-2 exhibited a degree of destruction of 100% after 7 days at an exemplary active compound concentration of 0.1%.

Example B
Spodoptera Test

| Solvent: | 7 parts by weight of | dimethylformamide |
|---|---|---|
| Emulsifier: | 1 part by weight of | alkylaryl polyglycol ether |

To prepare a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the owlet moth (*Spodoptera frugiperda*) while the leaves are still moist.

After the desired period time, the destruction in % is determined. 100% means that all the caterpillars have been killed; 0% means that none of the caterpillars have been killed.

In this test, for example the compound of Preparation Example I-2 exhibited a degree of destruction of 100% after 7 days at an exemplary active compound concentration of 0.1%.

Example C
Nephotettix Test

| Solvent: | 7 parts by weight of | dimethylformamide |
|---|---|---|
| Emulsifier: | 1 part by weight of | alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Rice seedlings (*Oryzae sativa*) are treated by being dipped into the preparation of the active compound of the desired concentration and are infested with larvae of the green rice leaf hopper (*Nephotettix cincticeps*) while the seedlings are still moist.

After the desired period of time, the destruction in % is determined. 100% means that all the leaf hoppers have been killed; 0% means that none of the leaf hoppers have been killed.

In this test, for example the compound of Preparation Example I-1 exhibited a degree of destruction of 100% after 6 days at an exemplary active compound concentration of 0.1%.

Example D

Myzus Test

| Solvent: | 7 parts by weight of | dimethylformamide |
|---|---|---|
| Emulsifier: | 1 part by weight of | alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) which are severely infested with the green peach aphid (*Myzus persicae*) are treated by being dipped into the preparation of the active compound of the desired concentration.

After the desired period of time, the destruction % is determined. 100% means that all the aphids have been killed; 0% means that none of the aphids have been killed.

In this test, for example the following compounds exhibited good activity:

TABLE D

| Active compound | Active compound concentration in % | Degree of destruction after 6 days |
|---|---|---|
| 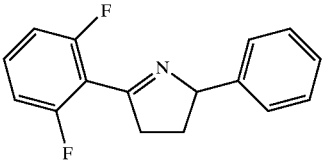<br>Example I-1 | 0.1 | 90 |
| 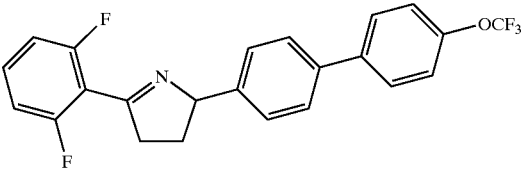<br>Example I-2 | 0.1 | 100 |

Example E
Tetranychus Test (OP Resistant/Dip Treatment)

| Solvent: | 3 parts by weight of dimethylformamide |
|---|---|
| Emulsifier: | 1 part by weight of alkylaryl polyglycol ether |

To prepare a suitable preparation of active compound, 1 part by weight of active compound is mixed with the stated amount of solvent and the stated amount of emulsifier, and the concentrate is diluted with emulsifier-containing water to the desired concentration.

Beans (*Phaseolus vulgaris*) which are strongly infested by all stages of the common spider mite (*Tetranychus urticae*) are dipped into an active compound preparation of the desired concentration.

After the desired time, the activity in % is determined. 100% means that all spider mites have been killed; 0% means that none of the spider mites have been killed.

In this test, for example the compound of Preparation Example I-2 exhibited a degree of destruction of 100% after 7 days at an exemplary active compound concentration of 0.001%.

Example F
Blow Fly Larvae Test/Development-Inhibitory Action

| Test animals: | All larval stages of *Lucilia cuprina* (OP resistant) [Pupae and adults (without contact with the active compound)] |
|---|---|
| Solvent: | 35 parts by weight of ethylene glycol monomethyl ether<br>35 parts by weight of nonylphenol polyglycol ether |

To prepare a suitable formulation, 3 parts by weight of active compound are mixed with 7 parts by weight of the abovementioned solvent-emulsifier mixture, and the resulting emulsion concentrate is diluted with water to the concentration desired in each case.

For each concentration, 30 to 50 larvae are transferred to horse meat (I cm$^3$) located in glass tubes, and 500 ill of the test dilution are pipetted onto the meat. The glass tubes are placed into plastic beakers whose bottom is covered with sea sand and kept in a controlled-environment cabinet (26° C.±1.5° C., 70% relative humidity ±10%). The activity is checked after 24 hours and 48 hours (larvicidal action). After the larvae have left (about 72 h), the glass tubes are removed and perforated plastic lids are placed on the beakers. After 1½ times the development period (hatching of the control flies), the hatched flies and the pupae/puparia are counted.

The criterion for the action is death in the treated larvae after 48 h (larvicidal effect), or inhibition of adults hatching from the pupae or inhibition of pupation The criterion for the in-vitro action of a substance is the inhibition of fly development or a standstill of development prior to the adult stage. 100% larvicidal activity means that all the larvae have died after 48 hours 100% development-inhibitory activity means that no adult flies have hatched.

In this test, for example the compound of Preparation Example I-1 exhibited an activity of 100% at an exemplary active compound concentration of 1000 ppm.

Example G

Ecdysis Test on Polyphargus Tick Nymphs

| | |
|---|---|
| Test animals: | *Amblyomma variegatium*, ticks which have sucked themselves full |
| Solvent: | 35 parts by weight of ethylene glycol monomethyl ether |
| | 35 parts by weight of nonylphenol polyglycol ether |

To prepare a suitable formulation, 3 parts by weight of active compound are mixed with 7 parts of the abovementioned solvent-emulsifier mixture, and the resulting emulsion concentrate is diluted with water to the concentration desired in each case.

10 Nymphs which have sucked themselves full are immersed for 1 minute into the preparation of active compound to be tested. The animals are transferred to Petri dishes (Ø 9.5 cm) equipped with filter paper discs and covered. After the nymphs have remained in a controlled-environment cabinet for 4 weeks, the ecdysis rate is determined.

100% means that all the animals have undergone normal ecdysis; 0% means that none of the animals have undergone normal ecdysis.

In this test, for example the compounds of Preparation Examples I-1 and I-2 showed an activity of in each case 100% at an exemplary active compound concentration of 1000 ppm.

What is claimed is:

1. A compound of the formula (I)

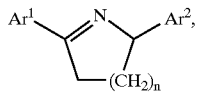

in which n represent, 2 or 3, $Ar^1$ represents the radical

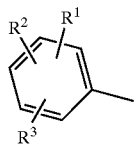

and $Ar^2$ represents the radical

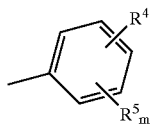

in which m represents 1, $R^1$ represents halogen, cyano, nitro, alkyl, alkoxy, halogenoalkyl, halogenoalkoxy, alkoxyalkyl, $R^2$ and $R^3$ independently of one another each represent hydrogen, halogen, cyano, nitro, alkyl, alkoxy, halogenoalkyl, halogenoalkoxy, alkoxyalkyl, $R^4$ represents the grouping —X—A  (l)

$R^5$ represents hydrogen, halogen, cyano, nitro, alkyl, alkoxy,

X represents a direct bond,

A represents phenyl, which is optionally mono- or polysubstituted by radicals from the list $W^1$,

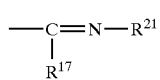  (e)

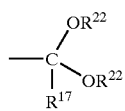  (f)

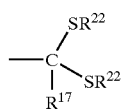  (g)

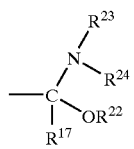  (h)

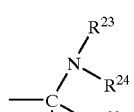  (i)

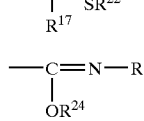  (j)

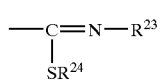  (k)

$W^1$ represents alkoxy, halogenoalkoxy, halogenoalkenyloxy.

2. The compound of claim 1 in which n represents 2, $Ar^1$ represents the radical

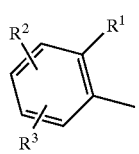

$Ar^2$ represents the radical

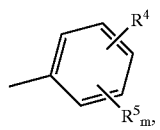

m represents 1, $R^1$ represents halogen, cyano, nitro, $C_1$–$C_6$-alkyl, $C_1$–$C_6$-alkoxy, $C_1$–$C_6$-halogenoalkyl or $C_1$–$C_6$-halogenalkoxy, represents $C_1$–$C_6$-alkyl, $R^2$ and $R^3$ independently of one another each represent hydrogen, halogen, cyano, nitro, $C_1$–$C_6$-alkyl, $C_1$–$C_6$-alkoxy, $C_1$–$C_6$-halogenoalkyl or $C_1$–$C_6$-halogenoalkoxy, represent $C_1$–$C_6$-alkyl, $R^4$ represents the grouping —X—A      (l)

$R^5$ represents hydrogen, halogen, cyano, nitro, $C_1$–$C_{16}$-alkyl, $C_1$–$C_{16}$-alkoxy, X represents a direct bond, A represents phenyl, which is mono-substituted by radicals from the list $W^1$,

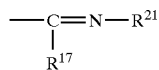      (e)

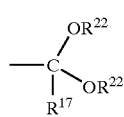      (f)

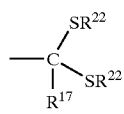      (g)

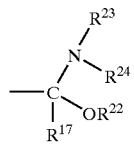      (h)

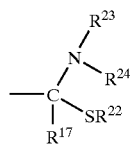      (i)

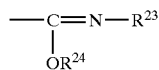      (j)

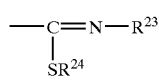      (k)

$W^1$ represents $C_1$–$C_{16}$-alkoxy, $C_1$–$C_6$-halogenoalkyl, $C_1$–$C_6$-halogenoalkoxy, $C_2$–$C_5$-halogenoalkenyloxy.

3. The compound of claim 1 in which n represents 2, $Ar^1$ represents the radical

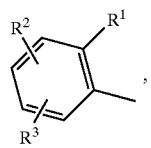

$Ar^2$ represents the radical

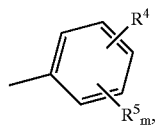

m represents 1, $R^1$ represents fluorine, chlorine, bromine, cyano, nitro, $C_1$–$C_6$-alkyl, $C_1$–$C_6$-alkoxy, respectively fluorine- or chlorine-substituted $C_1$–$C_6$-alkyl or $C_1$–$C_6$-alkoxy, represents $C_1$–$C_6$-alkoxy-$C_1$–$C_6$-alkyl, $R^2$ and $R^3$ independently of one another each represent hydrogen, fluorine, chlorine, bromine, cyano, nitro, $C_1$–$C_6$-alkyl, $C_1$–$C_6$-alkoxy, respectively fluorine- or chlorine-substituted $C_1$–$C_6$-alkyl or $C_1$–$C_6$-alkoxy, represent $C_1$–$C_6$-alkoxy-$C_1$–$C_6$-alkyl, $R^4$ represents the grouping —X—A      (l)

$R^5$ represents hydrogen, fluorine, chlorine, bromine, iodine, cyano, nitro, $C_1$–$C_{16}$-alkyl, $C_1$–$C_{16}$-alkoxy, X represents a direct bond, A represents phenyl, which is optionally mono-substituted by radicals from the list $W^1$,

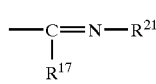      (e)

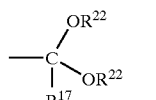      (f)

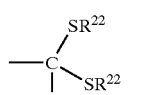      (g)

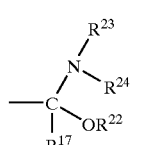      (h)

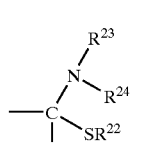      (i)

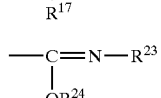      (j)

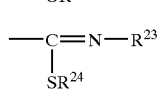      (k)

$W^1$ represents $C_1$–$C_4$-alkoxy, fluorine- or chlorine-substituted $C_1$–$C_4$-alkoxy.

4. The compounds of claim 1 in which n represents 2, $Ar^1$ represents the radical

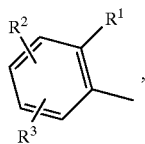

$Ar^2$ represents the radical

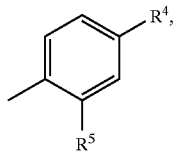

$R^1$ represents fluorine, chlorine, bromine, methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy, $R^2$ and $R^3$ independently of one another each represent hydrogen, fluorine, chlorine, bromine, methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy, $R^4$ represents the grouping

—X—A  (1)

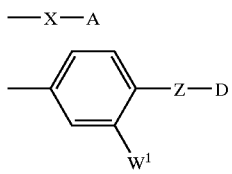  (m-a)

$R^5$ represents hydrogen, fluorine, chlorine, bromine, methyl, ethyl, methoxy, ethoxy, X represents a direct bond, A represents phenyl which is mono-substituted by radicals from the list $W^1$,

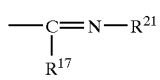  (e)

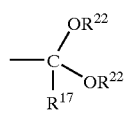  (f)

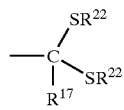  (g)

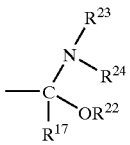  (h)

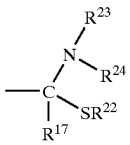  (i)

$W^1$ represents methoxy, ethoxy, n-propoxy, isopropoxy, n-butoxy, isobutoxy, sec-butoxy, tert-butoxy, trifluoromethoxy, difluoromethoxy, chlorodifluoromethoxy.

5. A compound of the formula (I-a)

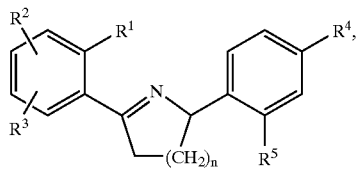  (I-a)

in which $R^1$, $R^2$, $R^3$, $R^5$ and n are each as defined in claim 1.

6. A pesticide composition comprising at least one compound of the formula (I) according to claim 1.

7. A method for controlling pests, comprising the step of allowing an effective amount of a compound of the formula (I) according to claim 1 to act on a member selected from the group consisting of said pests, a habitat of said pests and combinations thereof.

8. A process for preparing a pesticide formulation comprising the step of mixing a compound of the formula (I) according to claim 1 with a member selected from the group consisting of an extender, a surface-active agent and combinations thereof.

* * * * *